(12) United States Patent
Jessell et al.

(10) Patent No.: US 6,333,168 B1
(45) Date of Patent: *Dec. 25, 2001

(54) CLONING, EXPRESSION AND USES OF DORSALIN-1

(75) Inventors: Thomas M. Jessell, New York, NY (US); Konrad Basler, Kusnacht (CH); Toshia Yamada, Fort Lee, NJ (US)

(73) Assignee: The Trustees of Columbia University in the City of New York, New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/065,844

(22) Filed: May 20, 1993

(51) Int. Cl.[7] .................................................. C12P 21/02
(52) U.S. Cl. .................. 435/69.1; 435/320.1; 435/240.1; 435/325; 435/252.3; 536/23.1; 536/23.5
(58) Field of Search ................................ 435/69.1, 320.1, 435/240.1, 325, 348–366; 536/23.1, 23.5

(56) References Cited

U.S. PATENT DOCUMENTS 5,661,007 * 8/1997 Wozney et al. .................... 435/69.4

FOREIGN PATENT DOCUMENTS

| 8800205 | * 1/1988 | (WO) . |
| WO9011366 | 10/1990 | (WO) . |
| WO 93/00432 | 1/1993 | (WO) . |
| WO93/00432 | 1/1993 | (WO) . |

OTHER PUBLICATIONS

Basler, et al. (1993) "Control of cell pattern in the neural tube: regulation of cell differentiation by dorsalin–1, a novel TGF–β family member." *Cell* 73: 687–702.
Wozney, et al. (1988) "Novel regulators of bone formation: molecular clones and activities." *Science* 242: 1528–1534.
Ferguson et al., Cell, vol. 71, p. 451, 1992.*
Sambrook et al., Molecular Cloning, vol. 3, p. 16.2, 1989 Cold Spring Harbor Lab. Press.*
Kingsley et al., Genes & Development, 8:133–146, 1994.*
Lyons et al., Proc. Natl. Acad. Sci., vol. 86, pp. 4554–4558, 1989.*
Jakowlew et al., Molecular Endocrinology, vol. 2, pp 1186–1196, 1988.*

* cited by examiner

Primary Examiner—Lorraine Spector
Assistant Examiner—Eileen B. O'Hara
(74) Attorney, Agent, or Firm—John P. White; Cooper & Dunham LLP

(57) ABSTRACT

This invention provides an isolated vertebrate nucleic acid molecule which encodes dorsalin-1. This invention also provides a nucleic acid probe capable of specifically hybridizing with a sequence included within the sequence of a nucleic acid molecule encoding a dorsalin-1. The invention also provides a vector and host vector system for the production of a polypeptide having the biological activity of dorsalin-1 which comprises the above-described vector in a suitable host. This invention also provides a purified vertebrate dorsalin-1. This invention provides a method for stimulating neural crest cell differentiation, a method for regenerating nerve cells, a method for promoting bone growth, a method for promoting wound healing and a method for treating neural tumor using purified dorsalin-1. This invention further provides a pharmaceutical composition comprising purified dorsalin-1 and a pharmaceutically acceptable carrier. Finally, this invention provides an antibody capable of binding to dorsalin-1.

13 Claims, 16 Drawing Sheets

FIGURE 1

```
CCTTCCCTCTGTCTGTAAAGATTCAACATTTTAATCAGTTAAATACTTTGTCCCTCTGTCTCCATCAGAAAGTTAATACATAAGAA

M  H  Y  F  G  V  L  A  A  L  S  V  F  M  I  I  A  C  L  T  R  G  K  P  L  E  N  W  K  K
ATGCATTATTTTGGAGTGCTGGCACTGTCTGTCTTCAATATCATTGCCTGCCTGACAAGAGGCAAGCCTTTGGAAAACTGGAAAAAG    30

L  P  V  M  E  E  S  D  A  F  F  H  D  P  G  E  V  E  H  D  T  H  F  D  F  K  S  F  L  E
CTACCAGTTATGGAAGAGTCTGATGCATTCTTCCATGATCCTGGGGAAGTGGAACATGACACCCACTTTGACTTTAAATCTTTCTTGGAG   60

N  M  K  T  D  L  L  R  S  L  N  L  S  R  V  P  S  Q  V  K  T  K  E  E  P  P  Q  F  M  I
AATATGAAGACAGATTACTAAGAGTCTGAATTTATCAAGGGTCCCCTCACAAGTGAAGACCAAAGAAGAGCCACCACAGTTCATGATT     90

D  L  Y  N  R  Y  T  A  D  K  S  S  I  P  A  S  N  I  V  R  S  F  S  T  E  D  V  V  S  L
GATTTATACAACAGATATACAGCGGACAAGTCCTCCATCCCTGCATCCAACATCGTGAGGAGCTTCAGCACTGAAGATGTTGTTTCTTTA   120

I  S  P  E  E  H  S  F  Q  K  H  I  L  L  F  E  N  I  S  I  P  R  Y  E  E  V  T  R  A  E  L
ATTTCACCAGAAGAACACTCATTTCAGAAACACATCTGCTCTTCAACATCTCTATTCCACGATATGAGGAAGTCACCAGAGCTGAACTG    150

R  I  F  I  S  C  H  K  E  V  G  S  P  S  R  L  E  G  N  M  V  I  Y  D  V  L  D  G  D  H
AGAATCTTTATCTCCTGTCACAAGGAAGTTGGGTCTCCCTCCAGACTGGAAGGCAACATGGTCATTTATGATGTTCTAGATGGAGACCAT    180

W  E  N  K  E  S  T  K  S  L  L  V  S  H  S  I  Q  D  C  G  W  E  M  F  E  V  S  S  A  V
TGGGAAAACAAAGAAAGTACCAAATCTTTACTTGTCTCTCACAGTATTCAGGACTGTGGCTGGGAGATGTTTGAGGTGTCCAGCGCTGTG   210

K  R  W  V  K  A  D  K  M  K  T  K  N  K  L  E  V  V  I  E  S  K  D  L  S  G  F  P  C  G
AAAGATGGGTCAAGGCTCAAGACAAGATGAAGACTAAAAACAAGCTAGAGGTTGTTATAGAGAGTAAGGATCTGAGTGGTTTTCCTTGTGGG  240
```

FIGURE 1 (CONTINUED)

```
    K  L  D  I  T  V  T  H  D  T  K  N  L  P  L  L  I  V  F  S  N  D  R  S  N  G  T  K  E  T        270
    AAGCTGGATATTACTGTTACTCATGACACTAAAAATCGCCCTATTAATAGTGTTCTCCAATGATCGCAGCAATGGGACAAAAGAGACC

K  V  E  L  R  E  M  I  V  H  E  Q  E  S  V  L  N  K  L  G  K  N  D  S  S  E  E  E  Q        300
    AAAGTGGAGCTCCGGGAGATGATTGTTCATGAACAAGAAAGTGTGCTAAACAAATTAGGAAAGAACGACTCTTCATCTGAAGAAGAACAG

R  E  E  K  A  I  A  R  P  R  Q  H  S  S  R  S  K  R  S  I  G  A *N  H  C  R  R  T  S  L      330
    AGAGAAGAAAAAGCCATTGCTAGGCCCCGTCAGCATTCCTCCAGAAGCAAGAGAATAGGAGCATAGGAGCAAACCACTGTCGGAGAACGTCACTC

H  V  N  F  K  E  I  G  W  D  S  W  I  I  A  P  K  D  Y  E  A  F  E  C  K  G  G  C  F  F      360
    CATGTGAACTTCAAAGAAATAGGTTGGGATTCTTGGATCATTGCACCCAAAGATTATGAGGCTTTTGAGTGTAAAGGAGGTTGCTTCTTC

P  L  T  D  N  V  T  P  T  K  H  A  I  V  Q  T  L  V  H  L  Q  N  P  K  K  A  S  K  A  C      390
    CCCCTCACAGATAATGTACGCCAACAATGCTATTGTCCAGACTCTGGTCCATCTCCAAACCCAAAGAAAGCTTCCAAGGCCTGT

C  V  P  T  K  L  D  A  I  S  I  L  Y  K  D  D  A  G  V  P  T  L  I  Y  N  Y  E  G  M  K      420
    TGTGTTCCAACTAAATTGGATGCAATCTCTATTCTTTATAAGGATGATGCTGGTGTGCCCACTTGTGATATATAACTATGAAGGGATGAAA

V  A  E  C  G  C  R                                                                           427
    GTGGCAGAGATGTGGCTGCAGGTAGTATATGCTGAATATCTGAATATCTAAGAATATCTTTTCTGCTGTCGTGAAACTGTACATTAGTGATGCAA

ATGAAAATCCTTGCAAACAAGGTTTGGAGCACGGGACATGGGGCATGTGGTTGTTGTTGCTGCTTTAAGGAAAGATGGCATTAAAGAATGGC

AATCACTGTAAATACCCTGCATTATATACCATTAATTAAACTTTGTGAGATTGAAAAAAAAAAAAAAAAAAA
```

FIGURE 2A

```
DORSALIN-1   ..SVLNKLGKNDSSSEEQREEKAIARPRQHSSRSKR^SIGANHCRRTSLHVNF-KEIGWDSWIIAPKDYEAFECKGGCF
BMP-2        ..EHSWSQIRPLLVTFGHDGKGHPLHKREKRQAKHKQRKRLKSSCKRHPLYVDF--SDVGWNDWIVAPPGYHAFYCHGECP
DPP          ..DDGRHKARSIR^DVSGGEGGGKGRNKRHARRPTRRKNHDDTCRRHSLYVDF--SDVGWDDWIVAPLGYDAYYCHGKCP
BMP-6        ..RTTR^SASSRRRQQSRNRSTQSQDVARVSSADYNSSELKTACRKHELYVSF--QDLGWQDWIIAPKGYAANYCDGECS
VG-1         ..ECKDIQTFLYTSLLTVTLNPLRCKRPRKRSYSKLPFTASNICKKRHLYVEF--KDVGWQNWVIAPQGYMANYCYGECP
ACTIVIN-A    ..GADEEKEQSHRPFLMLQARQSEDHPHRRRR^GLECDGKVNICCKKQFFVSF-KDIGWNDWIIAPSGYHANYCEGECP
TGF-BETA-1   ..GMNRPFLLLMATPLERAQHLQSSRHRR^ALDTNYCFSSTEKNCCVRQLYIDFRKDLGWK-WIHEPKGYHANFCLGPCP    [427]
                                                                                              [396]
                                                                                              [588]
                                                                                              [514]
                                                                                              [360]
                                                                                              [427]
                                                                                              [390]

DORSALIN-1   FPLTDNVTPTKHAIVQTLVHLQ-----NPKKASKACCVPTKLDAISILYKDDAGVPTLIYNYEGMKVAECGCR
BMP-2        FPLADHLNSTNHAIVQTLVNSV-----N.SKIPKACCVPTELSAISMLYLDENEKVVLK--NYQDMWVEGCGCR
DPP          FPLADHFNSTNHAVVQTLVNNM-----NPGKVPKACCVPTQLDSVAMLYLNDQSTVVLK--NYQEMTVVGCGCR
BMP-6        FPLNAHMNALNHAIVQTLVHLM-----NPEYVPKPCCAPTKLNAISVLYFDDNSNVILK--KYRNMVVRACGCH
VG-1         YPLTEILNGSNHAILQTLVHSI-----EPEDIPLPCCVPTKMSPISMLFYDNNDNVVLR--HYENMAVDECGCR
ACTIVIN-A    SHIAGTSGSSLSFHSTVINHYRMRGHSPFANLKSCCVPTKLRPMSMLYYDDGQNIIKK--DIQNMIVEECGCS
TGF-BETA-1   -----YIWSLDTQYSKVLALY-NQHNPGASAAPCCVPQALEPLPIVYY-VGRKPKVE--QLSNMIVRSCKCS    [427]
                                                                                     [396]
                                                                                     [588]
                                                                                     [514]
                                                                                     [360]
                                                                                     [427]
                                                                                     [390]
```

FIGURE 4A 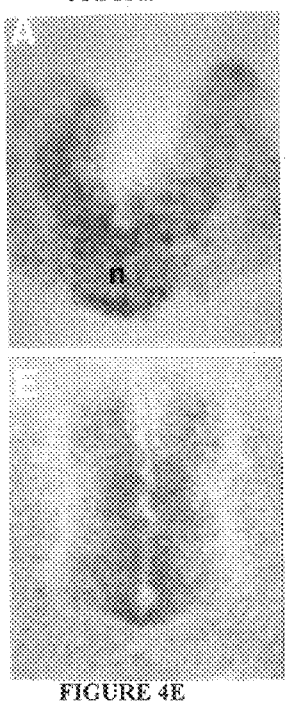 FIGURE 4B 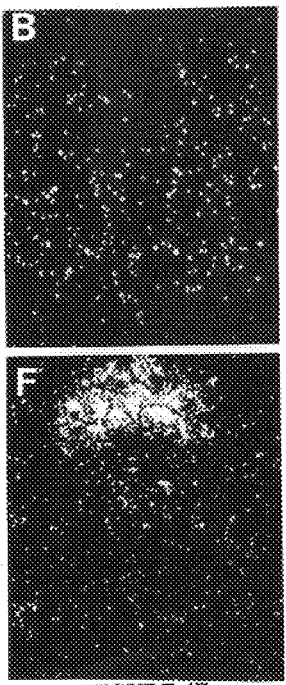 FIGURE 4C 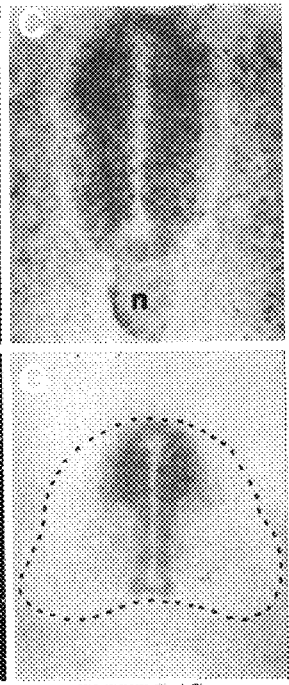 FIGURE 4D 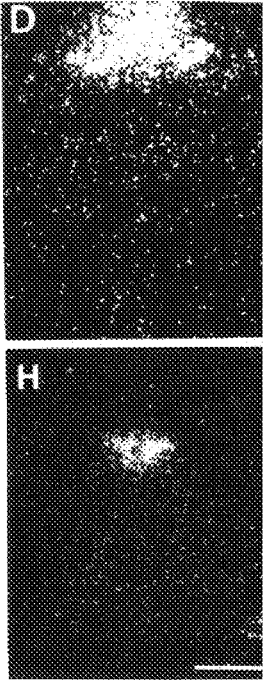
FIGURE 4E FIGURE 4F FIGURE 4G FIGURE 4H FIGURE 5G
FIGURE 5H
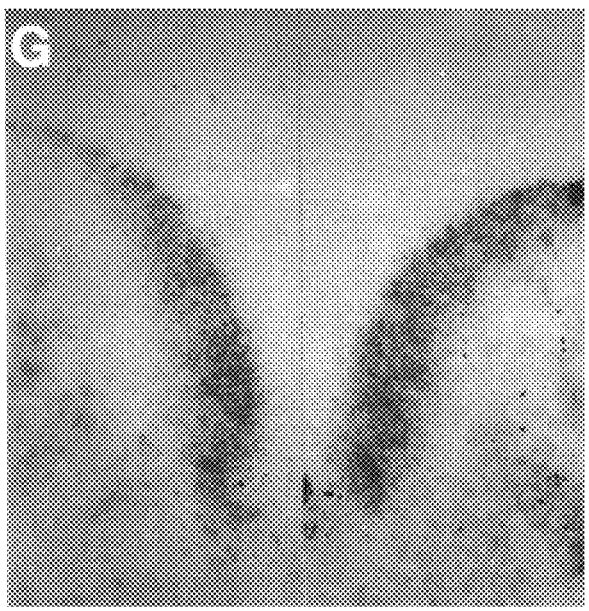
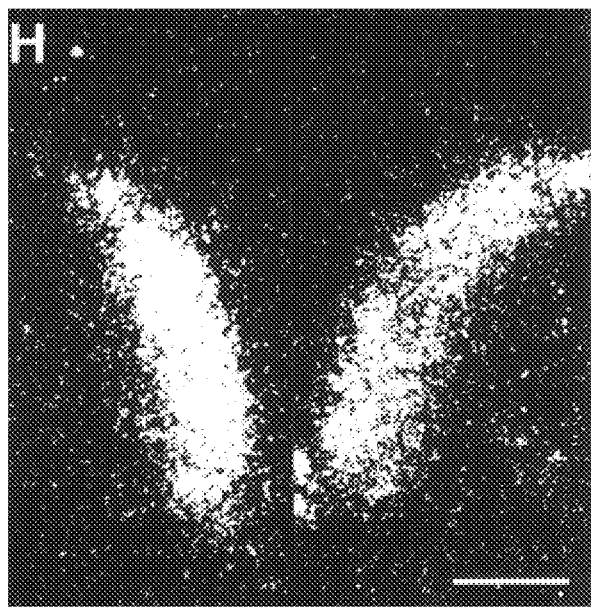

FIGURE 7G  FIGURE 7H  FIGURE 7I
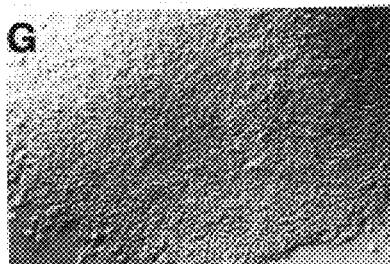 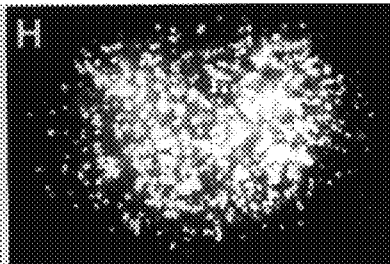 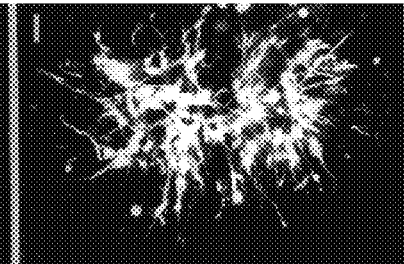
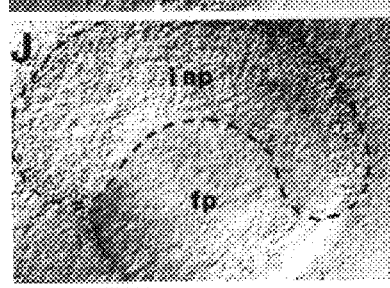 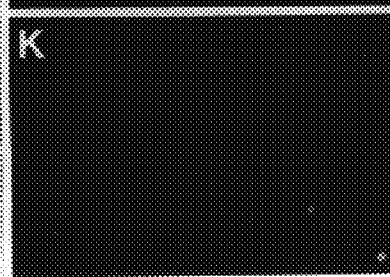 
FIGURE 7J  FIGURE 7K  FIGURE 7L

FIGURE 9A

A. ESTABLISHMENT OF *DORSALIN-1* EXPRESSION i) SIGNALS FROM THE NOTOCHORD SPECIFY THE VENTRAL FATE OF OVERLYING NEURAL PLATE CELLS

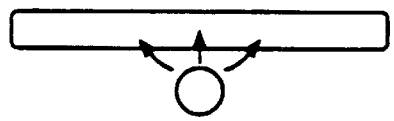

ii) SIGNALS FROM THE NOTOCHORD ACT ON OVERLYING NEURAL PLATE CELLS TO PREVENT SUBSEQUENT DSL-1 EXPRESSION

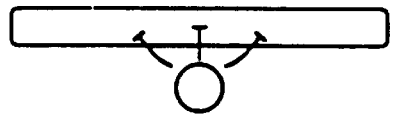

iii) RESTRICTED DORSAL EXPRESSION OF *DSL-1* OCCURS AFTER NEURAL TUBE CLOSURE

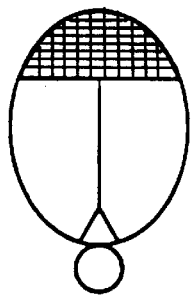

FIGURE 9B

B. POSSIBLE FUNCTIONS OF *DORSALIN-1* i) PROMOTION OF DORSAL CELL TYPE DIFFERENTIATION

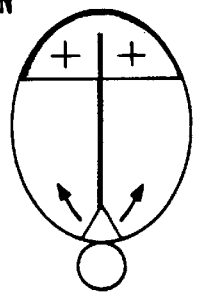

ii) LIMITING THE SPREAD OF VENTRAL SIGNALS

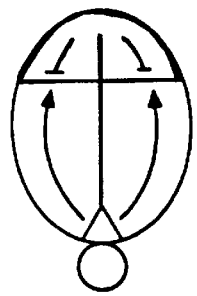

iii) DIFFUSION OF *DSL-1* CONTROLS CELL PATTERN MORE VENTRALLY

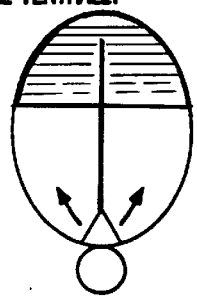

FIGURE 10

```
     1                                                                             80
B29  MHYFGVLAALSVFNIIACLTRGKPLENMKKLPVMEESDAFFHDPGEVEHDTHFDFKSFLENMKTDLLRSLNLSRVPSQVK
B29m ................................................................................

81                                                                            160
B29  TKEEPPQFMIDLYNRYTADKSSIPASNIVRSFSTEDVVSLISPEEHSFQKHILLFNISIPRYEEVTRAELRIFISCHKEV
B29m ................................................................................

161                                                                           240
B29  GSPSRLEGMVIYDVL.DGDHWENKESTKSLLVSHSIQDCGWEMFEVSSAVKRWVKADKMKTKNKLEVVIESKDLSGFPC
B29m .........DVLEDSETWDQATGTKTFLVSQDIRDEGWETLEVSSAVKRWVRADSTTNKNKLEVTVQSHRES...C 241                                                                           320
B29  GKLDITVTHDTKNLPLLIVFSNDRSNGTKETKVE.LREMIVHEQESVLNKLGKNDSSSEEEQREEKAI...ARPRQHSSR
B29m DTLDISVPPGSKNLPFFVVFSNDRSNGTKETRLDLLKEMIGHEQETMLVKTAKNAYQGAGESQEEEGLDGYTAVGPLLAR 321                                                                           400
B29  SKRSIGA.NHCRRTSLHVNFKEIGWDSWIIAPKDYEAFECKGGCFFPLTDNVTPTKHAIVQTLVHLQNPKKASKACCVPT
B29m RKRSTGASSHCQKTSLRVNFEDIGWDSWIIAPKEYDAYECKGGCFFPLADDVTPTKHAIVQTLVHLKFPTKVGKACCVPT 401                      433
B29  KLDAISILYKDDAGVPTLIYNYEGMKVAECGCR
B29m KLSPISILYKDDMGVPTLKYHYEGMSVAECGCR
```

CLONING, EXPRESSION AND USES OF DORSALIN-1

BACKGROUND OF THE INVENTION

Throughout this application various publications are referenced by the names of the authors and the year of the publication within parentheses. Full citations for these publications may be found at the end of the specification immediately preceding the claims. The disclosures of these publications in their entireties are hereby incorporated by reference into this application in order to more fully describe the state of the art to which this invention pertains.

Inductive interactions that define the fate of cells within the neural tube establish the initial pattern of the embryonic vertebrate nervous system. In the spinal cord, the identity of cell types is controlled, in part, by signals from two midline cell groups, the notochord and floor plate which induce neural plate cells to differentiate into floor plate, motor neurons and other ventral neuronal types (van Straaten et al. 1988; Placzek et al. 1990, 1993; Yamada et al. 1991; Hatta et al. 1991). The induction of floor plate cells appears to require a contact-mediated signal (Placzek et al. 1990a, 1993) whereas motor neurons can be induced by diffusible factors (Yamada et al., 1993). Thus, the fate of different ventral cell types may be controlled by distinct signals that derive from the ventral midline of the neural tube.

The specification of dorsal cell fates appears not to require ventral midline signals since the neural tube still gives rise to dorsal cell types such as sensory relay neurons and neural crest cells after elimination of the notochord and floor plate (Yamada et al. 1991; Placzek et al. 1991; Ericson et al. 1992). Moreover, dorsal cell types are found at more ventral positions in such embryos (Yamada et al. 1991; Placzek et al. 1991) suggesting that many or all cells in neural tube have acquired dorsal characteristics. The acquisition of a dorsal fate could represent a default pathway in the differentiation of neural plate cells or a response to inductive factors that are distinct from the ventralizing signals that derive from the notochord and floor plate.

To identify signals that might regulate cell differentiation within the neural tube, genes encoding secreted factors that are expressed in a restricted manner along the dorsoventral axis of the neural tube have been searched. In this application, the transforming growth factor β (TGF β) family have been focused since some of its members have been implicated in the control of cell differentiation and patterning in non-neural tissues. In frog embryos, for example, the differentiation and patterning of mesodermal cell types appears to be controlled, in part, by the action of activin-like molecules (Ruiz i Altaba and Melton, 1989; Green and Smith, 1990; Thomsen et al. 1990; Green et al. 1992). In addition, the dorsoventral patterning of cell types in Drosophila embryos is regulated by the decapentaplegic (dpp) gene (Ferguson and Anderson, 1992a,b). The dpp protein is closely related to a subgroup of vertebrate TGF β-like molecules, the bone morphogenetic proteins (BMPs) (Wozney et al. 1988), several members of which are expressed in restricted regions of the developing embryos (Jones et al. 1991). In this application, the cloning and functional characterization of the dorsalin-1 (dsl-1) gene, which encodes a novel BMP-like member of the TGF-β superfamily are described. Dsl-1 is expressed selectively by cells in the dorsal region of the neural tube and its expression in ventral regions appears to be inhibited by signals from the notochord. Dsl-1 promotes the differentiation or migration of neural crest cells and can prevent the differentiation of motor neurons in neural plate explants. The combined actions of dsl-1 and ventralizing factors from the notochord and floor plate may regulate the identity of neural cell types and their position along the dorsoventral axis of the neural tube.

SUMMARY OF THE INVENTION

This invention provides an isolated vertebrate nucleic acid molecule which encodes dorsalin-1. This invention also provides a nucleic acid probe comprising a nucleic acid molecule of at least 15 nucleotides capable of specifically hybridizing with a sequence included within the sequence of a nucleic acid molecule encoding a dorsalin-1.

The invention provides a vector which comprises an isolated nucleic acid molecule of dorsalin-1 operatively linked to a promoter of RNA transcription. This invention further provides a host vector system for the production of a polypeptide having the biological activity of dorsalin-1 which comprises the above-described vector in a suitable host.

This invention also provides a method of producing a polypeptide having the biological activity of dorsalin-1 which comprises growing the above-described host vector system under suitable conditions permitting production of the polypeptide and recovering the polypeptide so produced.

This invention also provides a purified vertebrate dorsalin-1. This invention further provides a purified human dorsalin-1.

This invention provides a method for stimulating neural crest cell differentiation in a subject comprising administering to the subject an amount of a purified dorsalin-1 effective to stimulate neural crest cell differentiation. This invention provides a method for regenerating nerve cells in a subject comprising administering to the subject an amount of a purified dorsalin-1 effective to regenerate nerve cells.

This invention provides a method for promoting bone growth in a subject comprising administering to the subject an amount of a purified dorsalin-1 effective to promote bone growth.

This invention provides a method for promoting wound healing in a subject comprising administering to the subject an amount of a purified dorsalin-1 effective to promote wound healing.

This invention provides a method for treating neural tumor in a subject comprising administering to the subject an amount of a purified dorsalin-1 effective to inhibit the tumor cell growth.

This invention further provides a pharmaceutical composition for stimulating neural crest cell differentiation comprising an amount of a purified dorsalin-1 effective to stimulate neural crest cell differentiation and a pharmaceutically acceptable carrier.

This invention provides a pharmaceutical composition for regenerating nerve cells in a subject comprising an amount of a purified dorsalin-1 effective to regenerate nerve cells and a pharmaceutically acceptable carrier.

This invention provides a pharmaceutical composition for promoting bone growth in a subject comprising an amount of a purified dorsalin-1 effective to promote bone growth and a pharmaceutically acceptable carrier.

This invention provides a pharmaceutical composition for promoting wound healing in a subject comprising an amount of a purified dorsalin-1 effective to promote wound healing and a pharmaceutically acceptable carrier.

This invention provides a pharmaceutical composition for treating neural tumor in a subject comprising an amount of a purified dorsalin-1 effective to inhibit neural tumor cell growth and a pharmaceutically acceptable carrier.

This invention provides an antibody capable of binding to dorsalin-1. This invention also provides an antibody capable of inhibiting the biological activity of dorsalin-1.

BRIEF DESCRIPTION OF FIGURES

FIG. 1 Nucleotide and Deduced Amino Acid Sequence of Dorsalin-1 (Seq. ID No. 1 and Seq. ID No. 2, respectively).

Figure 2B:
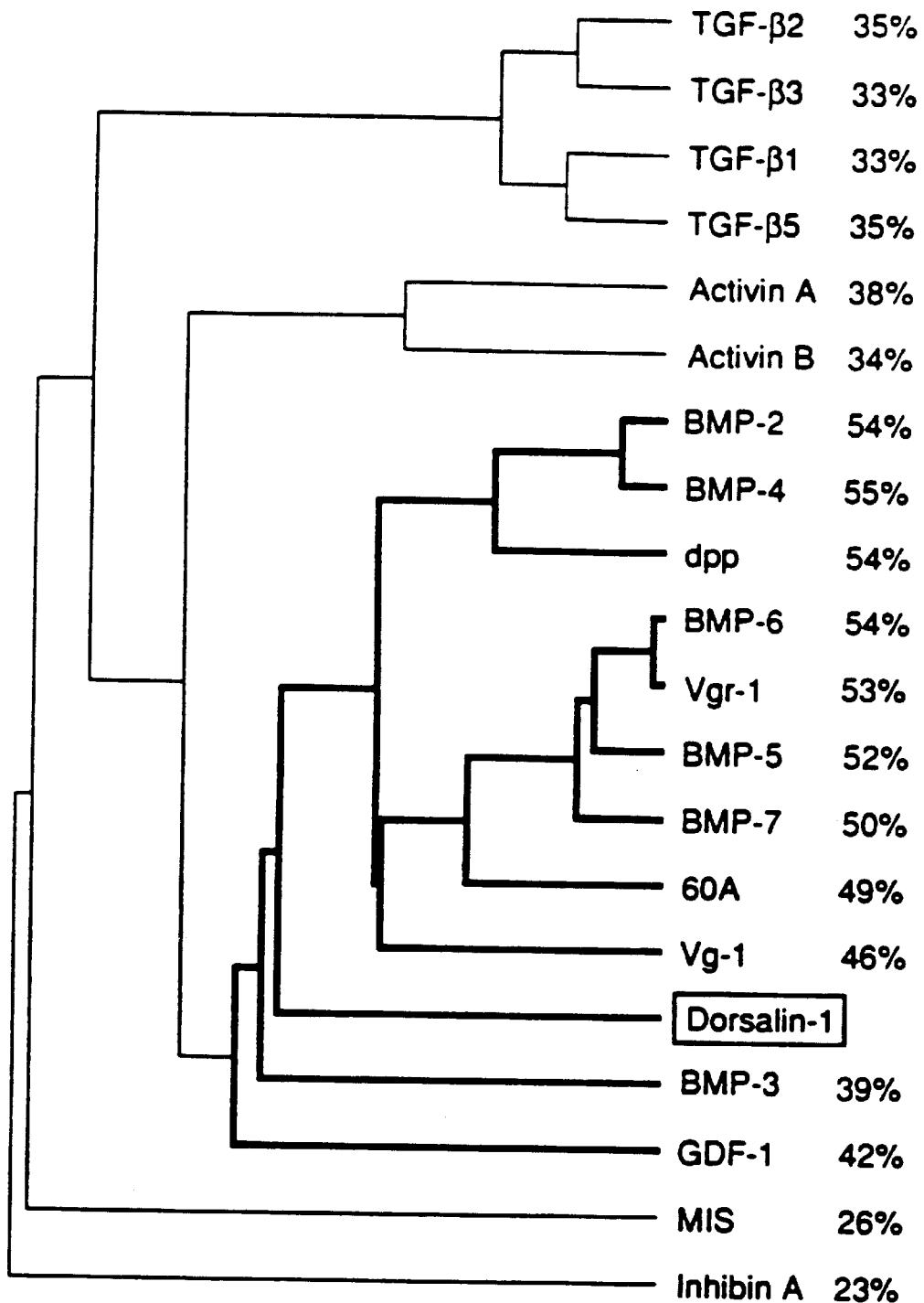

The numbering of the protein sequence starts with the first methionine of the long open reading frame. The putative signal sequence is typed in bold letters.

The RSKR (SEQ. ID No. 17) sequence preceding the proteolytic cleavage site (arrow) is underlined. The site of insertion of the 10 amino acid c-myc epitope is marked with an asterisk. The accession number for dorsalin-1 is L12032.

FIG. 2 Dorsalin-1 is a Member of the TGF-β Superfamily (A) Alignment of the COOH-terminal amino acid sequences of dorsalin-1 and some representative members of the TGF-β superfamily. Residues that are identical in at least 4 of the 7 proteins are printed in white on a black background. The 7 conserved cysteine residues are marked with an asterisk. Gaps introduced to optimize the alignment are represented by dashes. Known proteolytic cleavage sites in these proteins are marked with an arrow head. Numbers at the right indicate the number of amino acids present in the protein. Amino acid sequences of Dorsalin-1 (amino acids 284–427 of Seq. ID No. 2), BMP-2 (Seq. ID No. 3), DPP (Seq. ID No. 4), BMP-6 (Seq. ID No. 5), VG-1 (Seq. ID No. 6), Activin-A (Seq. ID No. 7) and TFG-Beta 1 (Seq. ID No. 8).

(B) Graphical representation of the sequence relationship between members of the TGF-β superfamily. This tree representation has been generated using the program pileup of the GCG software package (Devereeux et al., 1984). Underneath each branch the percentage amino acid identity is shown with reference to dorsalin-1. This value was calculated using the local homology algorithm of Smith and Waterman (1981) implemented in the program bestfit (GCG software). For both the tree and the amino acid identities only the sequence of the COOH-terminal domain was used, starting with the first of the seven conserved cysteine residues and ending with COOH-terminal residue. For details of other TGF-β family members see Lee (1990), Lyons et al. (1991), Hoffmann, (1991).

FIG. 3 Affinity Purification and Functional Activity of Recombinant Dorsalin-1 Protein (A) Dorsalin-1$^{myc}$ protein was purified from cos-7 cell-conditioned medium using a MAb 9E10 affinity column. An aliquot of the purified protein (CM) was run on a 15% SDS-polyacrylamide gel and stained with Coomassie Blue. The arrow points to the major product running at a molecular weight of ~15 kDa and minor bands at 45, 47 and 60 kDa are also evident. NH$_2$-terminal sequencing of the 15 kDa band confirmed its identity as processed dorsalin-1$^{myc}$ protein. Affinity-purified conditioned medium obtained from mock-transfected cos-7 cells did not contain any detectable protein on a Coomassie Blue stained acrylamide gel (not shown). The positions of molecular weight standards (MW) are shown.

(B) Induction of Alkaline Phosphatase Activity in W-20-17 Cells by Dorsalin-1. Conditioned medium was harvested from cos-7 transfected with dsl-1 cDNA, with the dSl-1$^{myc}$ cDNA and added at different dilutions to W20-17 cells for 72 h and alkaline phosphatase activity assayed (Thies et al. 1992). As a control for the presence of BMP-like activity in cos-7 cells, medium was also obtained from cells transfected with a c-myc tagged construct encoding the Drosophila decapentaplegic (dpp) gene, a related TGF β family member since (see FIG. 2B). Dpp$^{myc}$ is not detectable in the medium of transfected cos-7 cells. Curves are from one of three experiments that produced similar results. Recombinant human BMP-2 (Thies et al. 1992) was used as a positive control in the assay.

FIG. 4 Dorsalin-1 mRNA expression in the embryonic chick spinal cord

Panels represent pairs of phase-contrast and dark-field micrographs of sections of embryonic chick neural tube and spinal cord, processed for localization of dorsalin-1 mRNA by in situ hybridization with $^{35}$S-labelled probe.

(A,B) Dorsalin-1 mRNA is not expressed in neural cells at stages before neural tube closure. The dark field micrograph (B) shows background grain densities.

(C,D) Dorsalin-1 mRNA is expressed at high levels in the dorsal third of the neural tube, beginning at the time of neural tube closure, but not by ventral neural cells or by non-neural cells. This section is taken from a HH stage 10 embryo at the future brachial level.

(E,F) The dorsal restriction of dorsalin-1 mRNA persists in the spinal cord at stages after the onset of neuronal differentiation. Section taken from HH stage 22 embryo, at the brachial level.

(G,H) At later stages of spinal cord development (HH St 26) dorsalin-1 mRNA is restricted to the dorsomedial region of the spinal cord, including but not confined to the roof plate.

Scale bar: A,B=35 µm, C-F=80 µm, G-H=140 µm.

FIG. 5 Regulation of dorsalin-1 mRNA expression by notochord (A,B) Phase-contrast and dark-field images of a section of spinal cord from an operated stage 22 embryo but at a level in which there is no grafted tissue. The pattern of dorsalin-1 mRNA expression is similar to that in unoperated embryos at the same developmental age.

(C) Phase-contrast micrograph section from an embryo at the same stage as that shown in A,B, showing the expression of SC1 by motor neurons and floor plate cells, detected by immunoperoxidase histochemistry.

(D,E) Phase-contrast and dark-field images of a section of spinal cord from an operated stage 22 embryo in which there is a dorsally-located notochord (n). The expression of dorsalin-1 RNA is suppressed in the presence of a dorsal notochord graft. Similar results were obtained in 2 other embryos.

(F) Phase-contrast micrograph of an adjacent section to that shown in D,E, showing the ectopic dorsal location of SC1$^+$ motor neurons that form a bilaterally symmetric continuous column. SC1$^+$ motor axons can be seen leaving the dorsal spinal cord.

SC1$^+$ floor plate cells are detected at the dorsal midline. The position of the grafted notochord is indicated (n').

(G,H) Phase-contrast and dark-field micrographs showing that dorsal in-1 mRNA expression expands to occupy the entire neural epithelium in embryos from which Hensen's node has been removed at HH stage 10. In this embryo the operation resulted in a splitting of the neural tube and this micrograph has been spliced to restore the ventral apposition of neural tissue. Splitting of the neural tube occurs frequently after removal of Hensen's node (Darnell et al. 1992). A partial or complete ventral expansion of dsl-1 expression was detected in a total of 5 embryos with Hensen's node removal. A ventral expression of dsl-1 expression, occupying 60–70% of the spinal cord was also detected after notochord removal in 2 embryos.

Scale bar: A-F=90 μm, G-H=45 μm.

FIG. 6 Induction of Cell Migration from [i]-Neural Plate Explants by Dorsalin-1

[i]-Neural plate explants were grown alone or in the presence of dsl-$1^{myc}$ ($3 \times 10^{-11}$M) 48 h, and migratory cells analyzed by phase-contrast microscopy and by expression of surface antigens.

(A) Phase contrast micrograph of [i]-neural plate explant grown alone for 48 h.

(B) Phase contrast micrograph of [i]-neural plate explant grown in the presence of dsl-$1^{myc}$ for 48 h. Many cells have migrated from the explant.

(C) Phase contrast micrograph of an [i]-neural plate explant grown in contact with notochord (n) in the presence of dsl-$1^{myc}$ for 48 h. Cells still emigrate from the explant although few cells are located in the vicinity of the notochord explant.

(D) Expression of HNK-1 by cells induced to migrate from [i]-neural plate explant by dsl-$1^{myc}$.

(E) Expression of B1-integrin by cells induced to emigrate from [i]-neural plate explant. About 30% of migratory cells expressed p75, although the levels appeared lower than that detected on neural crest cells derived from the dorsal neural tube.

(F) Expression of melanin by cells induced to migrate from quail [i]-neural plate explants by dsl-$1^{myc}$. In these experiments dsl-$1^{myc}$ was removed from after 48 h and cultures grown in the presence of chick embryo extract (CEE) for a further 72 h. About 10–15% of cells in this bright field micrograph exhibit melanin pigment and typical dendritic morphology. Two different focal planes of the same field are shown to maintain melanocytes in focus. Similar results were obtained in 6–8 explants tested. For details see text.

(G) Quantitation of cell migration induced by dsl-1. [i]np indicates [i]-neural plate explant. nc=notochord, fp=floor plate. Error bars represent the means ±s.e.m. of migrated cells for 10–26 different explants.

Scale bar: A-C=70 μm, D-F=35 μm.

FIG. 7 Induction of Islet-1 expression in neural plate explants and suppression by dorsalin-1

(A–C) Normarski (A) and immunofluorescence (B,C) micrographs of stage 9-10 chick [i]-neural plate explant grown for 48 h in the absence of notochord or floor plate. Islet-$1^+$ cells are not detected (B) but there is extensive neuronal differentiation as detected by 3A10 expression (C).

(D-F) Nomarski (D) and immunofluorescence (E,F) micrographs of [i]-neural plate explant grown in contact with stage 26 chick floor plate. Numerous Islet-$1^+$ cells are present in the [i]-neural plate explant (np), but not in the floor plate explant (fp). The explant also contains many 3A10$^+$ cells (F).

(G-I) Nomarski (G) and immunofluorescence micrographs (H,I) of [i]-neural plate explant exposed for 48 h to floor plate-conditioned medium. Numerous Islet-$1^+$ cells (H) and 3A10$^+$ neurons (I) are detected.

(J-L) Nomarski (J) and immunofluorescence micrograph (K,L) of an [i]-neural plate and floor plate conjugate exposed for 48 h to $3 \times 10^{-11}$M dorsalin-$1^{myc}$. No Islet-$1^+$ cells are detected (K) whereas the number of 3A10$^+$ neurons in the neural plate explant (L) is not obviously different from that in the absence of dorsalin-$1^{myc}$. In figures D and G, the dashed line outlines the extent of the neural plate (np) explant.

Scale bar: A-C=70 μm, D-F=100 μm, G-I=70 μm, J-L=100 μm.

Figure 8A:
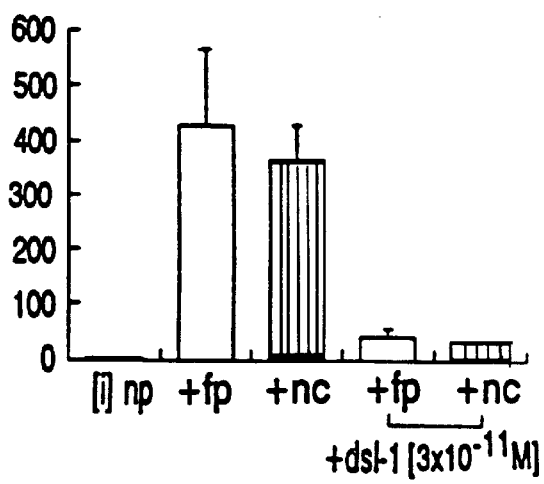

FIG. 8 Inhibition of Islet-$1^+$ Cells by Dorsalin-1

(A) Histograms showing the induction of Islet-$1^+$ cells in [i]-neural plate explants by contact with notochord (nc) or floor plate (fp), and the inhibition of Islet-$1^+$ cells by dorsalin-$1^{myc}$ ($3 \times 10^{-11}$M). Each column represents mean ±s.e.m. of 10–22 different explants.

(B) Dose-dependent inhibition of Islet-1+cells by dorsalin-$1^{myc}$. Each point represents mean ±s.e.m. of 7–23 different explants.

(C) Induction of Islet-$1^+$ cells by floor plate-conditioned medium and the inhibitory action of dorsalin-$1^{myc}$. Each column represents mean ±s.e.m. of 7–23 explants.

[i]np=[i]-neural plate explant grown alone, +nc=neural plate/notochord conjugate, +fp=neural plate/floor plate conjugate, fpcm=floor plate-conditioned medium.

FIG. 9 Potential Functions of Dorsalin-1 in the Control of Cell Differentiation in the Neural Tube Diagrams summarize the possible mechanisms for establishing the dorsally-restricted expression of dorsalin-1 and potential functions of dorsalin-1 in the regulation of cell differentiation along the dorsoventral axis of the neural tube.

(A) The pattern dorsalin-1 expression appears to be established by early signals from the notochord. (i) Medial neural plate cells respond to signals from the underlying notochord which induce the differentiation of ventral cell types such as floor plate and motor neurons. (ii) Medial neural plate cells are also exposed to signals from the notochord that prevent the subsequent expression of dorsalin-1. The inhibitory signal from the notochord can, in principle, be identical to the ventralizing signal that induces ventral cell fates. (iii) The medial region of the neural plate gives rise to the ventral neural tube. Dorsalin-1 expression (shaded area) begins at the time of neural tube closure and is restricted to the dorsal third of the neural tube.

(B) In vitro assays suggest several possible functions for dorsalin-1 in the control of neural cell differentiation. (i) Dorsalin-1 may promote the differentiation of cell types that derive from the dorsal region of the neural tube. In vitro studies suggest that neural crest cells represent one population of cells whose differentiation may be influenced by dorsalin-1. (ii) The dorsal expression of dorsalin-1 may define the dorsal third of the neural tube as a domain that is refractory to the long range influence of ventralizing signals from the notochord and floor plate. The ventral boundary of dorsalin-1 expression suggests that ventral midline-derived signals can influence cells over much of the dorsoventral axis of the neural tube. (iii) Dorsalin-1 protein may diffuse ventrally to influence the fate of cells in intermediate regions of the neural tube beyond the domain of dorsalin-1 MRNA expression. Thus, the combined action of dorsalin-1 and the diffusible ventralizing signal from the notochord and floor plate could specify the fate of cells over the complete dorsoventral axis of the neural tube.

FIG. 10 Amino acid comparison of chick dorsalin-1 (B29) (Seq. ID No. 2) and mouse (B29m) (Seq. ID No. 9).

DETAILED DESCRIPTION OF THE INVENTION

This invention provides an isolated vertebrate nucleic acid molecule encoding dorsalin-1. As used herein, the term dorsalin-1 encompasses any amino acid sequence, polypeptide or protein having the biological activities provided by dorsalin-1.

In one embodiment of this invention, the isolated nucleic acid molecules described hereinabove are DNA. In a further embodiment, isolated nucleic acid molecules described hereinabove are cDNAs or genomic DNAs. In the preferred embodiment of this invention, the isolated nucleic sequence is cDNA as shown in sequence ID number 1. In another embodiment, the isolated nucleic acid molecule is RNA.

This invention also encompasses DNAs and cDNAs which encode amino acid sequences which differ from those of dorsalin-1, but which should not produce phenotypic changes. Alternatively, this invention also encompasses DNAs and cDNAs which hybridize to the DNA and CDNA of the subject invention. Hybridization methods are well-known to those of skill in the art.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian host; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecules are useful for generating new cloning and expression vectors, transformed and transfected procaryotic and eucaryotic host cells, and new and useful methods for cultured growth of such host cells capable of expression of the polypeptide and related products.

Moreover, the isolated nucleic acid molecules are useful for the development of probes to study the neurodevelopment.

Dorsalin-1 may be produced by a variety of vertebrates. In an embodiment, a human dorsalin-1 nucleic acid molecule is isolated. In another embodiment, a mouse dorsalin-1 nucleic acid molecule is isolated. In a further embodiment, a chick dorsalin-1 nucleic acid molecule is provided. The plasmid, pKB502, encoding a chick dorsalin-1 was deposited on Oct. 5, 1992 with the American Type Culture Collection (ATCC),10801 University Boulevard Manassas, Va. 20110-2209, U.S.A. under the provisions of the Budapest Treaty for the International Recognition of the Deposit of Microorganism for the Purposes of Patent Procedure. Plasmid, pKB502 was accorded ATCC Accession number 75321.

Throughout this application, references to specific nucleotides are to nucleotides present on the coding strand of the nucleic acid. The following standard abbreviations are used throughout the specification to indicate specific nucleotides:

C=cytosine
A=adenosine
T=thymidine
G=guanosine

For the purpose of illustration only, applicants have isolated and characterized dorsalin-1 cDNA clones from chicken and mouse. Similar techniques are applicable to isolate and characterize the dorsalin-1 genes in different vertebrates.

Dorsalin-1 genes may be isolated using the probe generated from the chick dorsalin-1 gene. The mouse and human homologous genes may be cloned by using probe from the chick gene by low stringency screening of the correspondent embryonic spinal cord cDNA libraries. A mouse dorsalin-1 was cloned using the above method. FIG. 10 shows a mouse homolog of the dorsalin-1 which reveals extensive conservation at the nucleotide and amino acid level with the chick dorsalin-1. The human dorsalin-1 is likely to be more closely related to the mouse protein than is the chick protein. Thus, it should be straightforward to design oligonucleotide primers to isolate the human dorsalin-1 gene.

This invention provides a nucleic acid molecule comprising a nucleic acid molecule of at least 15 nucleotides capable of specifically hybridizing with a sequence included within the sequence of a nucleic acid molecule encoding a dorsalin-1. The above molecule can be used as a probe. As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes dorsalin-1 into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

The probes are useful for 'in situ' hybridization or in order to locate tissues which express this gene, or for other hybridization assays for the presence of this gene or its mRNA in various biological tissues.

Vectors which comprise the isolated nucleic acid molecule described hereinabove also are provided. Suitable vectors comprise, but are not limited to, a plasmid or a virus. These vectors may be transformed into a suitable host cell to form a host cell vector system for the production of a polypeptide having the biological activity of dorsalin-1.

This invention further provides an isolated DNA or CDNA molecule described hereinabove wherein the host cell is selected from the group consisting of bacterial cells (such as E. coli), yeast cells, fungal cells, insect cells and animal cells. Suitable animal cells include, but are not limited to Vero cells, HeLa cells, Cos cells, CV1 cells and various primary mammalian cells.

This invention provides a method to identify and purify expressed dorsalin-1. A myc-epitope was introduced into dorsalin-1. This myc carrying dorsalin-1 was linked to an expression vector. Such vector may be used to transfect cell and the distribution of dorsalin-1 in the cell may be detected by reacting myc antibodies known to be reactive to the introduced myc-epitope with the transfected cells which is expressing the dorsalin-1 carrying myc-epitope. Taking advantage of this myc-epitope, dorsalin-1 may be purified by an antibody affinity column which binds with this myc-epitope.

In one embodiment, the expression vector, pKB501 (with myc epitope), containing chick dorsalin-1 with a myc-epitope was deposited on Oct. 5, 1992 with the American Type Culture Collection (ATCC),10801 University Boulevard Manassas, Va. 20110-2209, U.S.A. under the provisions of the Budapest Treaty for the International Recognition of the Deposit of Microorganism for the Purposes of Patent Procedure. Plasmid, pKB 501 (with myc epitope) was accorded ATCC designation number 75320.

The above uses of the myc-epitope for identification and purification of dorsalin-1 should not be considered limiting only to the myc-epitope. Other epitopes with specific antibodies against them which are well known to an ordinary skilled in the art could be similarly used.

Also provided by this invention is a purified vertebrate dorsalin-1. As used herein, the term "purified vertebrate dorsalin-1"shall mean isolated naturally-occurring dorsalin-1 or protein (purified from nature or manufactured such that the primary, secondary and tertiary conformation, and posttranslational modifications are identical to naturally-occurring material) as well as non-naturally occurring polypeptides having a primary structural conformation (i.e. continuous sequence of amino acid residues). Such polypeptides include derivatives and analogs. In one embodiment, the purified dorsalin-1 is human dorsalin-1.

This invention also provides polypeptides encoded by the above-described isolated vertebrate nucleic acid molecules.

This invention provides a method for stimulating neural crest cell differentiation in a culture comprising administering an amount of the above-described purified dorsalin-1 effective to stimulate neural crest cell differentiation to the culture.

This invention also provides a method for stimulating neural crest cell differentiation in a subject comprising administering to the subject an amount of the above-described purified dorsalin-1 effective to stimulate neural crest cell differentiation.

This invention provides a method for regenerating nerve cells in a subject comprising administering to the subject an effective amount of the above-described purified dorsalin-1 effective to regenerate nerve cells.

This invention provides a method for promoting bone growth in a subject comprising administering to the subject an effective amount of the above-described purified dorsalin-1 effective to promote bone growth.

This invention provides a method for promoting wound healing in a subject comprising administering to the subject an effective amount of above-described purified dorsalin-1 effective to promote wound healing.

This invention provides a method for treating neural tumor in a subject comprising administering to the subject an amount of the above-described purified dorsalin-1 effective to inhibit the tumor cell growth. In an embodiment, the neural tumor is neurofibroma. In another embodiment, the neural tumor is Schwann cell tumor.

This invention also provides a method for preventing differentiation of motor neurons in a culture comprising administering an amount of purified dorsalin-1 neurons to the culture.

This invention also provides a method for preventing differentiation of motor neurons in a subject comprising administering to the subject an amount of the above-described dorsalin-1 effective to prevent differentiation of motor neurons.

This invention also provides a pharmaceutical composition for stimulating neural crest cell differentiation comprising an amount of purified dorsalin-1 of claim 18 effective to stimulate neural crest cell differentiation and a pharmaceutically acceptable carrier.

As used herein, "pharmaceutically acceptable carriers" means any of the standard pharmaceutically acceptable carriers;. Examples include, but are not limited to, phosphate buffered saline, physiological saline, water and emulsions, such as oil/water emulsions.

This invention provides a pharmaceutical composition for regenerating nerve cells in a subject comprising an amount of the above-described purified dorsalin-1 effective to regenerate nerve cells and a pharmaceutically acceptable carrier.

This invention provides a pharmaceutical composition for promoting bone growth in a subject comprising an amount of the above-described purified dorsalin-1 effective to promote bone growth and a pharmaceutically acceptable carrier.

This invention provides a pharmaceutical composition for promoting wound healing in a subject comprising an amount of the above-described purified dorsalin-1 effective to promote wound healing and a pharmaceutically acceptable carrier.

This invention provides a pharmaceutical composition for treating neural tumor in a subject comprising an amount of the above-described purified dorsalin-1 effective to inhibit neural tumor cell growth and a pharmaceutically acceptable carrier. In an embodiment of this pharmaceutical composition, the neural tumor is neurofibroma. In another embodiment of this pharmaceutical composition, the neural tumor is Schwann cell tumor.

Also provided by this invention is a method to produce antibody using the above-described purified dorsalin-1. Standard procedures for production of antibodies against dorsalin-1 are well-known to an ordinary skilled artisan. A procedure book, entitled "Antibodies, A Laboratory Manual" (1988) by Ed Harlow and David Lane (published by Cold Spring Harbor Laboratory) provides such standard procedures. The content of "Antibodies, A Laboratory Manual" is hereby incorporated in this application.

This invention further provides antibody capable of binding to dorsalin-1. In an embodiment, the antibody is monoclonal.

This invention further provides an antibody against dorsalin-1 capable of inhibiting the biological activity of dorsalin-1.

This invention further provides a method for inhibiting dorsalin-1 activity in a subject comprising administering to the subject an amount of an antibody capable of inhibiting dorsalin-1 activity effective to inhibit the dorsalin-1 activity.

This invention also provides a pharmaceutical composition for inhibiting dorsalin-1 activity comprising an amount of antibody capable of inhibiting dorsalin-1 activity effective to inhibit dorsalin-1 activity and a pharmaceutically acceptable carrier.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Experimental Procedures

RNA Isolation and PCR Amplification

Spinal cord tissue was dissected from 80 embryonic day (E) 2.5 chicks. Poly (A)$^+$ RNA (20 $\mu$g) was isolated from this tissue using an oligo (dT)-cellulose spin column (Pharmacia®) and 1.5 µg was used in two first strand cDNA synthesis reactions with either oligo (dT) or random hexanucleotides as primers for the reverse transcriptase reaction. One third of each of the two cDNA reaction mixture was combined and used as template for PCR amplification using 100 pmoles of the following degenerate primers in a reaction volume of 50 µl:

5'TG<u>GAATTC</u>TGG(ACG)A(ACGT)GA(CT)TGGAT(ACT)(AG)T(ACGT)GC 3'(SEQ ID No. 10) and 5'GA<u>GGATCC</u>A(AG)(ACGT)GT(CT)TG(ACGT)AC(AGT)AT(ACGT)GC(AG)TG 3'(SEQ ID No. 11)

where degenerate positions are in parenthesis and restriction sites underlined. These oligonucleotides correspond to the dorsalin-1 amino acid positions 339–345 and 377–371, respectively. The reaction was cycled twice between 94° (50 seconds), 50° (2 minutes), and 72° (2 minutes), followed by 28 rounds of 94° (50 seconds), 55° (2 minutes), and 72° (1.5 minutes). The reaction products were purified, digested with BamHI and EcoRI, size selected by agarose gel electrophoresis and cloned into the bacteriophage vector M13mp18. 50 clones were picked randomly and analyzed on a sequencing gel by comparing their G ladders. One member of each class was sequenced completely.

DNA Isolation and Sequencing

An E2.5 chick spinal cord CDNA library of $10^6$ independent clones was constructed in lambda ZAPII (Stratagene®) using 5 µg of the poly(A)+ RNA described above. After amplifying the library, $10^6$ clones were screened under standard hybridization conditions and a $^{32}$P-labeled PCR probe derived from the 116 bp insert of M13 clone B29 representing the dorsalin-1 class. Of approximately 25 positive clones, 4 were plaque-purified and converted into pBluescript plasmids. Sequence analysis was performed by a combination of primer walking and subcloning of small restriction fragments into M13. The sequence within and adjacent to the long open reading frame was determined on both strands by the dideoxy chain termination method (Sanger et al. 1977) using SequenaseS (U.S. Biochemicals).

DNA Constructs

The coding region of dorsalin-1 was isolated using the two PCR primers ORF-5' (5' TGGAATTCATCGATAACG-GAAGCTGAAGC 3'; SEQ ID No. 12) and ORF-3' (5' AGCGTCGACATCGATATTCAGCATATACTACC 3'; SEQ ID No. 13) and cloned into pBS SK-between the EcoRI and SalI sites. To insert the c-myc epitope (EQKLISEEDL; SEQ. ID No. 18) two internal primers, each encoding half of the c-myc epitope and dorsalin sequences from the epitope insertion site (see FIG. 1), were used to produce two PCR fragments, one encoding dorsalin N-terminal to the insertion site (with primer ORF-5' and the primer 5' GCGAATTC-<u>GATAT</u>CAGCTTCTGCTCTGCTCCTATGCTTCTCTTGC 3' [SEQ. ID No. 14]) and the other encoding the C-terminal region with primer 5' CGGAATTC<u>GATAT</u>CCGAGGAGGACCTGAACCACTGTCGGAGAA CGTC 3'; SEQ ID No. 15 and primer ORF-3'). These two fragments were joined using their primer-derived EcoRV sites and cloned the same way as the unmodified coding region. Using nearby primers this region was sequenced to confirm that no other mutations had been introduced.

A truncated coding region was derived from this construct by cleavage with HindIII, blunting the ends with T4 DNA polymerase and subsequent religation. This leads to a frameshift mutation which replaces the C-terminal 41 residues of dorsalin with 9 unrelated ones. The unmodified, the epitope-tagged and the truncated dorsalin coding regions were then cloned into the Cos-7 cell expression vector pMT21 between the EcoRI and XhoI sites.

In Situ Hybridization Histochemistry

A dorsalin-1 cDNA clone was linearized with XbaI (at amino acid position 176) and used to generate a 1 kb [$^{35}$S]UTP-labeled antisense RNA probe using T7 RNA polymerase. This probe encompasses the 3' part of the cDNA. Chick embryos were fixed in 4% paraformaldehyde and 10 µm cryostat sections were mounted on 3-aminopropyltriethoxysilane-treated slides. In situ hybridization was performed essentially as described by Wilkinson, et al. (1987) with exposure times ranging from 4 to 10 days. The distribution of dorsalin-1 mRNA was confirmed by whole-mount in situ hybridization, performed essentially as described by Harland (1991) using a digoxygenin-11-UTP-labeled RNA probe derived from the template mentioned above (not shown).

Chick Embryo Manipulations

Notochord grafting and deletion in ovo was performed as described by Yamada et al. (1991). For removal of Hensen's; node from stage 9–10 chick embryos in ovo, the embryo was visualized by injection of India ink underneath the cavity between the yolk and embryo. Hensen's; node was cut out together with underlying endoderni using fine tungsten needles. After the operation, the window was sealed and the embryo was incubated for further 48 h at 37° C. in the humidified incubator. Embryos were then fixed with 4% paraformaldehyde overnight at 4° C. and embedded in paraffin for in situ hybridization as described above.

Cos-7 Cell Transfections

Cos-7 cells were transfected by the DEAE-Dextran method as described by Klar, et al. 1992). For small scale cultures 60 to 100 µm dishes were used and conditioned medium was prepared by incubating cells expressing dorsalin-1 for 48 h in 3 or 6 ml of OPTI-MEM (BRL®), respectively. Large-scale transfections for affinity-purification of dorsalin-1 comprised 15×150 mm dishes for transfection with dorsalin$^{myc}$ DNA (bearing the myc epitope) and an equal number of dpp or mock-transfected plates. This yielded 150 ml of dorsalin$^{myc}$ conditioned medium and 150 ml of cos-7 conditioned control medium. The BMP-4 expression plasmids was provided by R. Derynck.

Affinity Purification and Sequence Analysis of dorsalin-1$^{myc}$

Conditioned medium (50 ml) containing dsl-1$^{myc}$ was clarified by centrifugation at 30,000×q and affinity-purified on 1 ml of a monoclonal 9E10 (anti-myc) antibody coLumn (Affi-Gel, Biorad®). Dsl-1$^{myc}$ protein was eluted with 0.1 M glycine-HCI (pH 2.5) and immediately neutralized with 3 M Tris base. The eluate was concentrated and desalted over a 2 ml Centricon-10 microconcentrator (Amicon). The protein concentration of the final fraction (volume approximately 130 µl), as determined by amino acid analysis, was 0.1 µg/ml.

For SDS-polyacrylamide gel electrophoresis, 10 µl of concentrated protein was loaded on a 15% Biorad Mini-Protean II gel and stained with Coomassie Blue. 60 µl was used on a preparative gel and blotted onto Immobilon membrane in the absence of glycine. The blot was stained briefly with Coomassie Blue and the major band at 15 kD was excised and subjected to N-terminal protein sequencing on a Applied Biosystems 470A gas phase sequencer/120A PTH analyzer. The minor protein migrating slightly slower on the gel (at 16.5 kD) was also sequenced and had the identical N-terminus, suggesting that it is an alternately glycosylated form of dsl-1. Affinity-purified conditioned medium from mock-transfected cos-7 cells did not contain any detectable protein on a Coomassie-stained acrylamide gel.

The concentration of dorsalin-$1^{myc}$ used for bioassays was determined on the assumption that all activity resides in the ~15 kDa band which represents about 50% of the protein recovered after affinity-purification. The total protein in the affinity-purified fraction determined by amino acid analysis was found to be 100 ng/µl, of which 50 ng/µl is assumed to represent active protein. The stock concentration of Dsl-$1^{myc}$ was therefore $3 \times 10^{-6}$M. This stock was then diluted $10^5$ fold for most assays to give a final condition of $3 \times 10^{-11}$M, assuming negligible losses.

Islet-1 Induction Assay

The assay for induction of Islet-1+ cells was carried out as described in detail in Yamada et al. 1993. [i]-Neural plate explants were isolated from Hamburger Hamilton HH stage 10 chick embryos (Yamada et al. 1993) and grown in collagen gels alone or with HH stage 10 notochord, HH stage 26 floor plate or with floor plate-conditioned medium in F12-N3 defined culture medium (Tessier-Lavigne et al. 1988) at 37° C. for 48 to 120 h. Floor plate-conditioned medium was obtained by culturing 30 HH stage 25–26 floor plate fragments in 1 ml of F12 N3 medium for 48 h.

After incubation, explants were fixed with 4% paraformaldehyde at 4° C. for 1–2 h, washed with PBS at 4° C. and gently peeled from the bottom of the dish and excess collagen gel was trimmed. Explants were incubated with primary antibodies overnight at 4° C. with gentle agitation. Rabbit anti-Islet-1 antibodies (Thor et al. 1991, Ericson et al. 1992) and MAb SC1 (Tanaka and Obata, 1984) were used for detection of differentiating motor neurons and MAb 3A10 as a general neuronal marker (Dodd et al., 1988). After washing with PBS for 2 h at 22° C., the explants were incubated with Texas Red conjugated goat anti-rabbit antibodies (Molecular Probes) or FITC-conjugated goat anti-mouse Ig (Boehringer Mannheim) for 1–2 h. Explants were washed with PBS at 22° C. for 2 h with at least two changes of buffer and mounted on slides in 50% glycerol with paraphenylene diamine (1 mg/ml). The number of Islet-$1^+$ and 3A10$^+$ cells was determined on a Zeiss Axiophot microscope equipped with epifluorescence optics. Double labeling with anti-Islet-1 and anti-SCI antibodies was analyzed using BioRad confocal microscope.

Analysis of Neural Crest Differentiation

[i]-Neural plate explants from stage 10 chick embryos were grown in collagen gels as described for analysis of Islet-1 induction. The number of migratory cells was determined by phase-contrast microscopy. Cells were scored as migratory if they were greater than two cell body diameters away from the mass of the [i]-neural plate explant. Identification of surface antigens was performed on cultures fixed with 4% paraformaldehyde using MAb 7412 against chick p75 (Tanaka et al. 1989); MAb HNK1 (Abo and Balch, 1981), and MAb JG22 (anti-β1 integrin; Greve and Gottlieb, 1982). For analysis of melanocyte differentiation, [i]-neural plate explants were isolated from HH st. 10 quail (Coturnix coturnix japonica) embryos as described for equivalent chick explants (Yamada et al. 1993) and grown in vitro in collagen gels. Explants were treated with dsl-$1^{myc}$ ($3 \times 10^{11}$M) for 48 h in F12-N3 medium at which time the medium was removed, explants washed and placed in F12-N3 medium containing 10% chick embryo extract and 10% fetal calf serum for a further 72 h. Dsl-1 was removed after 48 h because members of the TGF β family have been found to inhibit the differentiation of neural crest cells into melanocytes (Stocker et al., 1991; Roger et al. 1992). CEE and serum were added after 48 h to permit the differentiation of neural crest cells into melanocytes (Barofio et al. 1988; Maxwell et al. 1988). Dorsal neural tube and [i]-neural plate explants grown in dsl-$1^{myc}$ for 48 h followed by defined medium lacking CEE or serum for a further 72 h gave rise to few, if any, melanocytes. Thus the presence of CEE and serum appears necessary to support melanocyte differentiation under these conditions. When CEE and serum was included in the medium from the onset of culture, cells migrated from [i]-neural plate explants and after 120 h, melanocytes were observed.

To prepare chick embryo extract, white leghorn chicken eggs were incubated for 11 days at 38° C. in a humidified atmosphere. Embryos were removed and homogenized in minimal essential medium by passage through a 30 ml syringe, stirred at 40° C. for 1 h, and then centrifuged for 5 h at 30,000×g. The supernatants was collected, filtered and stored at −80° C. until used.

Alkaline Phosphatase Induction in W-20-17 Cells

Induction of alkaline phosphatase activity by dsl-1 was assayed in W-20-17 cells as described (Thies et al. 1992) using recombinant human BMP-2 as a positive control.

Results

Isolation and Characterization of Dorsalin-1

Degenerate oligonucleotides directed against conserved sequences present in the subfamily of TGF-β members that includes the BMPs, Vg1 and dpp were used to isolate novel members of the TGF-β family (Wharton et al., 1991). Oligonucleotides were used as primers in a polymerase chain reaction (PCR) to amplify sequences derived from HH stage 16–18 (embryonic day 2.5) chick spinal cord cDNA. The PCR products were cloned and 37 of 50 clones had inserts encoding Vg-1/dpp/BMP-related peptides. Although most clones encoded chick homologues of previously characterized BMP genes, one class encoded a novel sequence. A 116 bp fragment encoding this sequence was used as probe to screen an E 2.5 chick spinal cord cDNA library and to define a clone containing a 3.5 kb insert with an open reading frame that encoded a protein of 427 amino acids (FIG. 1).

The predicted amino acid sequence identifies this protein, dorsalin-1 (dsl-1), as a new member of the TGF-β superfamily. The N-terminal domain of dsl-1 contains a stretch of hydrophobic residues that could serve as a signal sequence. A comparison of COOH-terminal 109 amino acids with those of other members of this family reveals that dsl-1 contains most of the conserved amino acids present in the other family members, including seven characteristic cysteine residues (FIG. 2A). The structure of TGF-β2 (Daopin et al., 1992; Schlunegger and Grutter, 1992) suggests that in dsl-1, intrachain disulfide bonds are formed between cysteines 7 and 73, 36 and 106, 40 and 108, and that cysteine 72 is involved in dimer stabilization through formation of an interchain disulfide bond. The $NH_2$ terminal domain of the dsl-1 precursor does not exhibit any significant similarity to other members of the TGF-β family.

Dsl-1 is more related to members of the Vg-1/dpp/BMP subfamily than to the TGF-β, activin or MIS subfamilies (FIG. 2B). Given the high degree of sequence conservation of individual members of the BMP family identified in different species (FIG. 2), the divergence in sequence between dsl-1 and mammalian TGF-β family members suggests that the dsl-1 gene encodes a novel member of this superfamily. The sequence of the mouse dsl-1 gene (Cox and Basler, unpublished findings) supports this idea.

As with other family members, the conserved COOH-terminal region is immediately preceded by a series of basic residues that could serve as a site for proteolytic cleavage of the precursor protein (Celeste et al., 1990; Barr, 1991). An epitope-tagged derivative, dsl-1$^{myc}$, which contains a 10 amino acid insert derived from the human c-myc proto-oncogene (Evan et al., 1985) was generated to determine the site of cleavage of the dsl-1 precursor. The c-myc sequence was inserted two residues upstream of the first conserved cysteine in a region of the protein that exhibits no conservation with other members of the TGF-β family (FIG. 2A). cDNAs encoding native and epitope-modified dsl-1 were cloned into the expression vector pMT 21 and transfected separately into cos-7 cells.

Figure 3A:
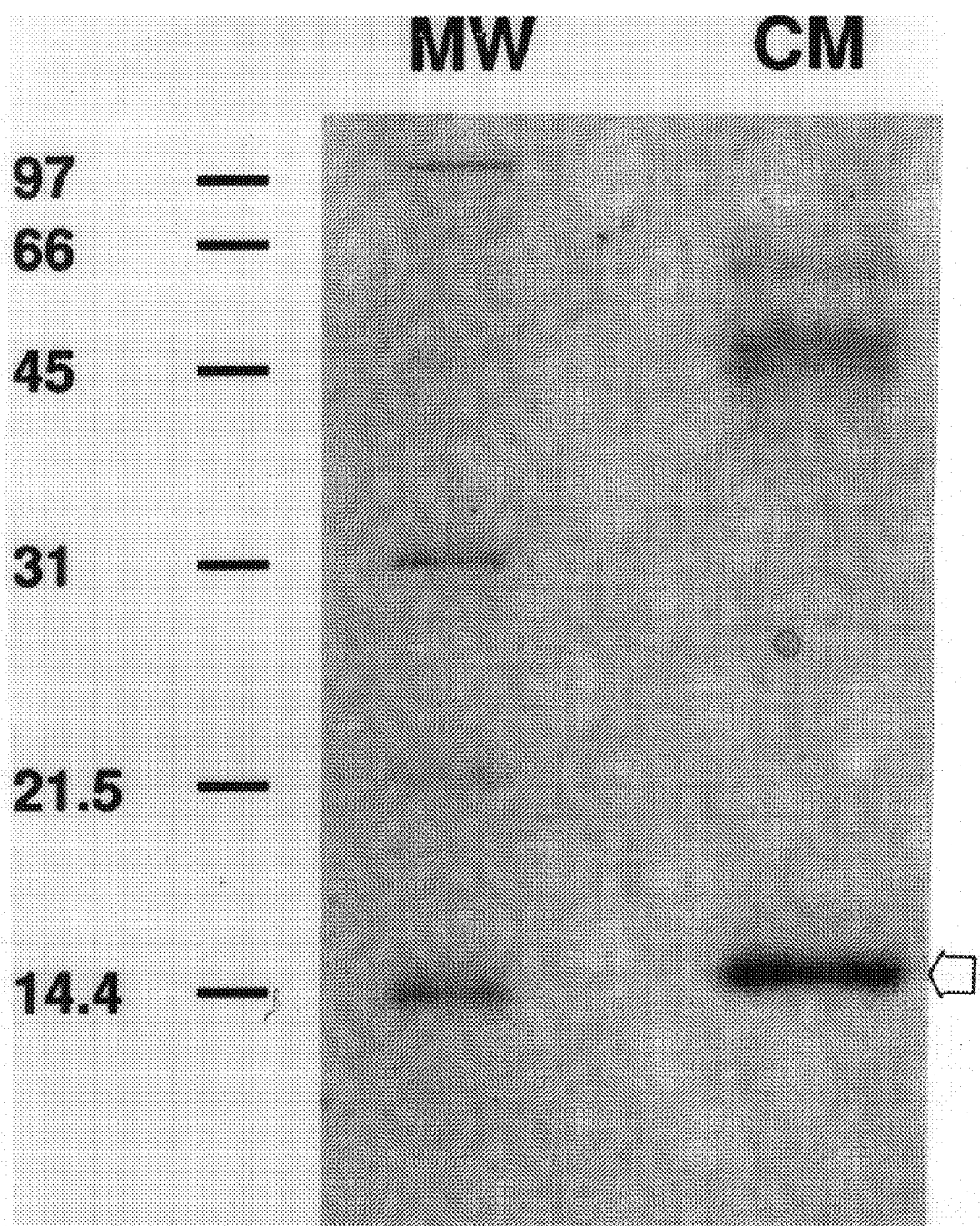

Medium from cells transfected with the epitope-modified dsl-1 construct was passed over a MAb 9E10 (Evan et al., 1985) anti c-myc affinity column. Affinity purified proteins were analyzed by gel electrophoresis, revealing a major 15 kDa band and minor bands at 45,47 and -60 kDa (FIG. 3A). The bands at 45 and 47 kDa correspond in size to those predicted for the unproceesed dsl-1 protein and the 15 kDa band to that expected for a proteolytically-cleaved product. To establish the identity of the 15 kDa band and to determine the site for proteolytic cleavage of the precursor protein, the 15 kDa band was blotted onto Immobilon membranes and subjected to sequence analysis. The $NH_2$-terminal sequence obtained, SIGAEQKLIS (SEQ ID No. 16), corresponds to residues 319–322 of the predicted. dsl-1 sequence followed by the first 6 residues of the human c-myc epitope. This result shows that the R-S-K-R (SEQ ID No. 17) sequence at residues 315–318 is the site of proteolytic processing of the dsl-1 precursor (arrow in FIG. 1), at least in the presence of the c-myc peptide.

Figure 3B:
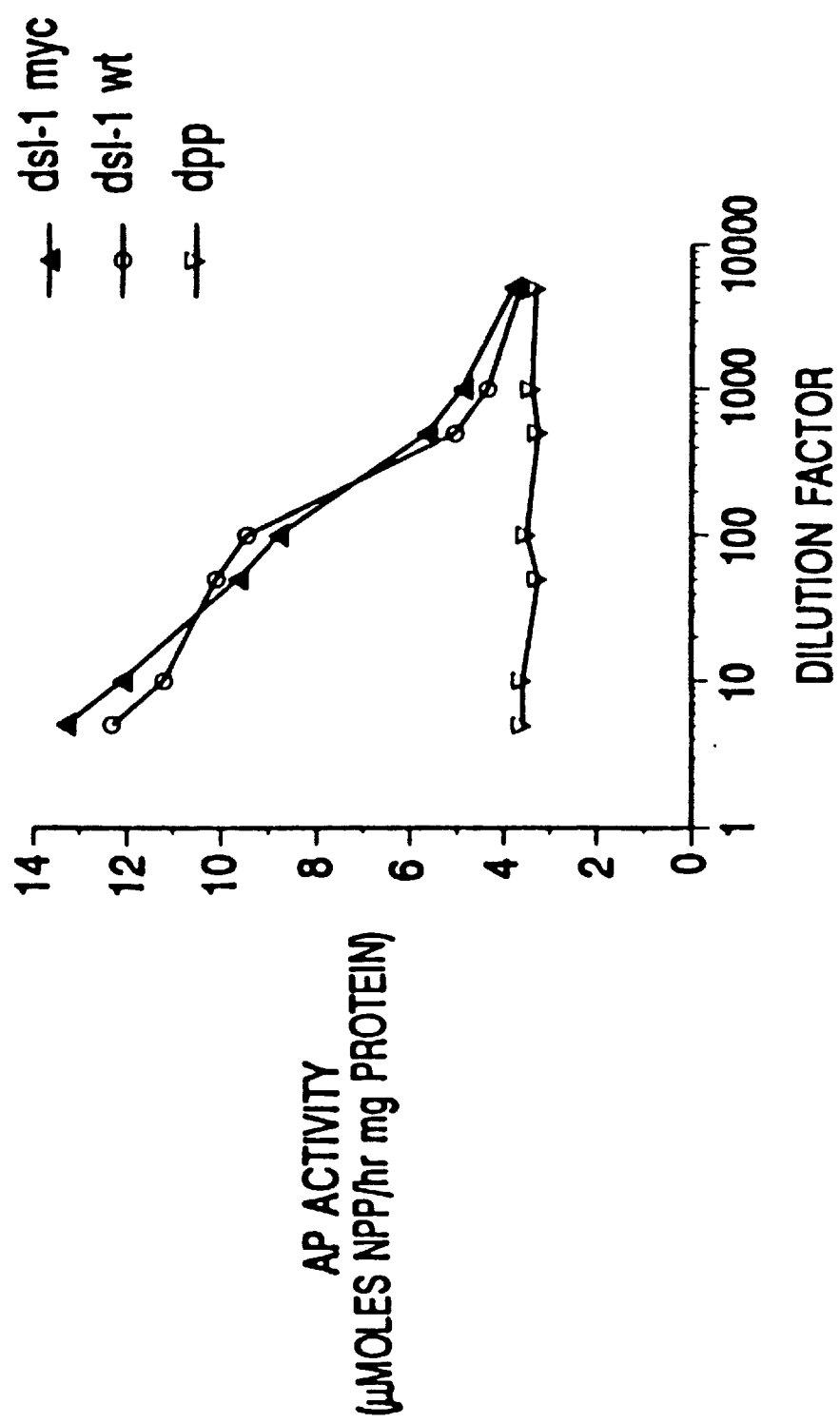

To determine whether recombinant dsl-1 secreted by cos-7 cells has BMP-like activity, a biochemical assay of osteoblast differentiation was used in which BMPs induce alkaline phosphatase activity (Thies et al. 1992). Recombinant BMP-2 produced a dose-dependent increase in alkaline phosphatase activity in W-20-17 osteoblast cells over a concentration range of 10-1000 ng/nl (not shown; Thies et al. 1992). Conditioned-medium obtained from cos-7 cells transfected with dsl-1 produced an increase in alkaline phosphatase similar to that of BMP-2 at dilutions of 1:10 to 1:1000 (FIG. 3B). Moreover, medium derived from cos-7 cells transfected with dsl-1$^{myc}$ cDNA, was effective as medium derived from cells transfected with unmodified dsl-1 cDNA (FIG. 3B). In control experiments, cos-7 cells were transfected with a c-myc tagged version of the Drosophila decapentaplegic (dpp) gene, which encodes a related TGF-8 family member (FIG. 2b). Cos-7 cells do not secret dpp protein (Basler, unpublished observations) and medium derived from dpp transfectants did not induce alkaline phosphatase activity, providing evidence that cos-7 cells subjected to the same transfection protocol do not secrete a BMP-like activity (FIG. 3B). These results show that dsl-1 can be expressed in cos-7 cells in functional form, that dsl-1 mimics the activity of BMPs in this assay and that the activity of dsl-1 is not reduced by insertion of the c-myc peptide.

Expression of dsl-1 RNA in the Developing Nervous System

Dsl-1 mRNA was localized in developing chick embryos by in situ hybridization to examine the expression of dsl-1 during neural development. Dsl-1 mRNA was not expressed by cells in the neural plate (FIGS. 4A,B) and first appeared at the time of closure of the neural tube. At this stage, dsl-1 was expressed at high levels in the dorsal third of the neural tube but was absent from more ventral regions (FIGS. 4C,D). Dsl-1 mRNA was restricted to the nervous system at this stage of development (not shown).

The restricted expression of dsl-1 mRNA in the spinal cord persisted after the onset of neuronal differentiation (FIGS. 4E–F), and by E5, the latest stage examined, the domain of expression of dsl-1 mRNA was confined to the dorsomedial region of the spinal cord including, but not restricted to, the roof plate (FIGS. 4G,H). Dsl-1 mRNA was also expressed in dorsal regions of the hindbrain after neural tube closure (not shown). From E3 to E5, the only non-neural tissue types that expressed detectable levels of dsl-1 mRNA were kidney and myotomal cells (not shown) although the level of mRNA expression in these tissues was much lower than that in the nervous system.

Regulation of Dsl-1 Expression by the Notochord

Figure 5A:
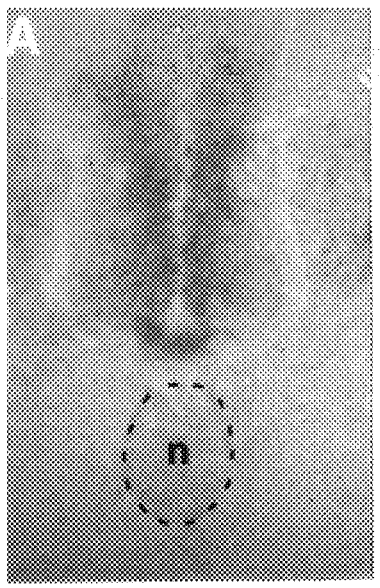
Figure 5B:
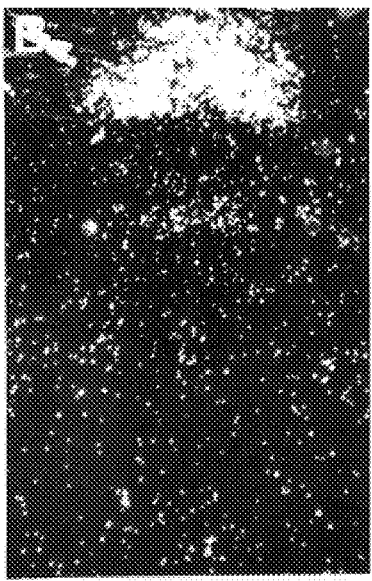
Figure 5C:
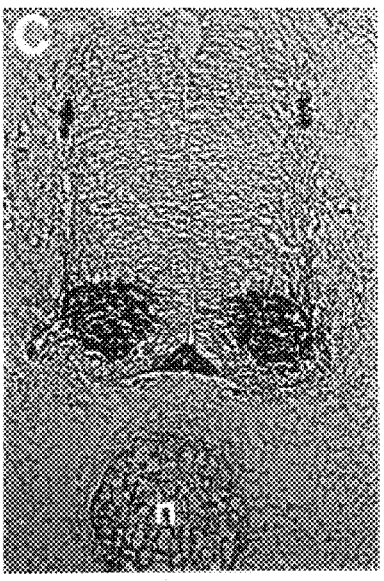
Figure 5D:
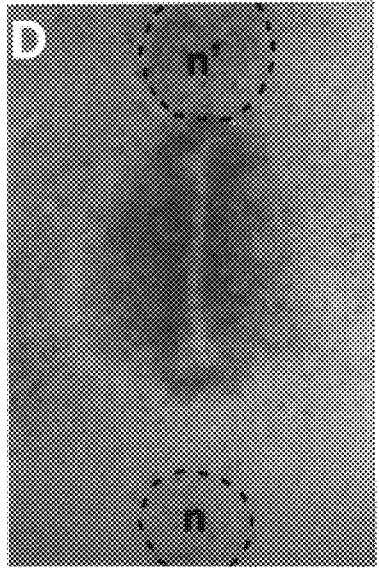
Figure 5E:
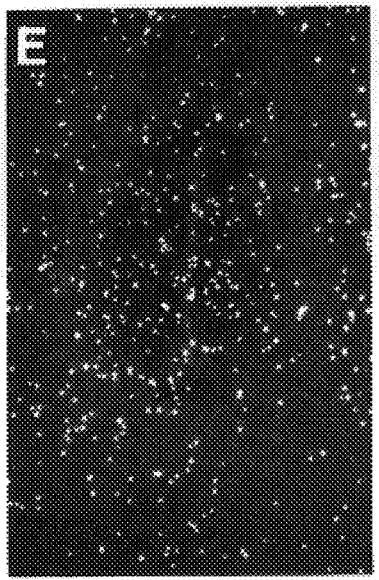

The expression of antigenic markers that are restricted to dorsal neural tube cells is regulated by signals from the notochord and floor plate (Yamada et al. 1991; Placzek et al. 1991) raising the possibility that dsl-1 mRNA expression is controlled in a similar manner. To examine this possibility, segments of stage 10 chick notochord were grafted into the lumen of the neural groove of host embryos prior to the onset of dsl-1 mRNA expression. Embryos were incubated for a further 48 h, during which time the graft was displaced dorsally, such that it is eventually located at the dorsal midline of the neural tube and spinal cord. Dsl-1 mRNA expression, determined by in situ hybridization, was absent from the spinal cord of embryos with dorsal notochord grafts (FIGS. 5D,E) whereas the spinal cord of operated embryos at rostrocaudal levels that were not adjacent to the dorsal notochord graft exhibited the normal pattern of dsl-1 mRNA expression (FIGS. 5A,B).

Figure 5F:
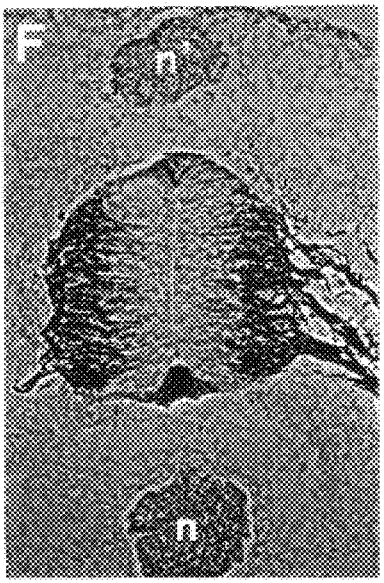

To correlate changes in dsl-1 mRNA expression with neural cell pattern, sections of operated embryos adjacent to those used for in situ hybridization were examined for expression of SC1, an immunoglobulin-1like protein present on floor plate cells and motor neurons (FIG. 5C) (Tanaka and Obata, 1984; Yamada et al., 1991). In embryos in which dsl-1 mRNA was absent from the spinal cord, SC1 expression revealed the presence of dorsal motor neurons and sometimes a floor plate at the dorsal midline of the spinal cord (FIG. 5F). Thus, dorsal notochord grafts abolish the expression of dsl-1 mRNA and ventralize the dorsal spinal cord.

The ability of the notochord to inhibit dsl-1 mRNA expression suggests that the notochord might normally have a role in restricting the expression of dsl-1 within the neural tube. Elimination of ventral midline-derived signals might therefore result in an expansion in the domain of dsl-1 expression. To test this, Hensen's node, the precursor of the notochord, was removed from stage 10 chick embryos, thus preventing the formation of the notochord and ensuring that an early source of ventral midline-derived signals (Yamada et al. 1993) is eliminated prior to neural tube formation. The spinal cords of such embryos have been shown to lack a floor plate and ventral neurons (Grabowski, 1956; Hirano et al., 1991; Darnell et al. 1992; Yamada, unpublished). In embryos from which Hensen's node had been removed, the domain of dsl-1 mRNA expression expanded ventrally, and in extreme cases included the entire dorsoventral extent of the neuroepithelium (FIGS. 5G,H). In a second series of experiments, the notochord was removed from the caudal region of stage 10 embryos, which were then permitted to develop for an additional 48 h. At levels of the spinal cord lacking a floor plate and motor neurons, as assessed by SC1 labelling, the domain dsl-1 expression expanded ventrally to occupy about two thirds of the spinal cord, although, the most ventral region never expressed dsl-1 (not shown). The more limited ventral expansion of dsl-1 observed after removal of the notochord compared with Hensen's node removal is consistent with other studies (Yamada et al. 1993) suggesting that ventralizing signals from the notochord begin to act soon after the neural plate has formed.

Taken together, these experiments suggest that the expression of dsl-1 mRNA in ventral regions of the neural tube is normally inhibited by signals from the notochord.

Dsl-1 Regulates Neural Differentiation In Vitro

The dorsal restriction of dsl-1 mRNA suggests two ways in which dsl-1 protein could regulate cell differentiation along the dorso-ventral axis of the neural tube. One function of dsl-1 could be to promote the differentiation of cell types generated in the dorsal neural tube. A second function of dsl-1 could be to counteract the influence of ventralizing signals that derive from the notochord and floor plate. The actions of dsl-1 on the differentiation of defined cell types in neural plate explants grown in vitro have been examined to test the possible functions of dsl-1. In the following sections, we provide evidence first that dsl-1 can promote the differentiation of cells with neural crest-like properties and second that dsl-1 can inhibit the differentiation of motor neurons in response to inductive signals from the notochord and floor plate.

Neural Crest Cell Differentiation

Neural crest cells are generated from precursors located in the dorsal neural tube (Bronner-Fraser and Fraser, 1988). They can be identified in vitro by their ability to migrate from the neural tube, by their expression of several cell surface markers including the HNK-1 epitope (Maxwell et al. 1988), β1 integrin (Delannet and Duband, 1992), the low-affinity neurotrophin receptor subunit p75 (Bernd, 1985; Stemple and Anderson, 1992) and by their ability to differentiate into cell types such as neurons, glial cells and melanocytes (Sieber-Blum and Cohen 1980; Baroffio et al, 1988; Stocker et al. 1991).

Figure 6A:
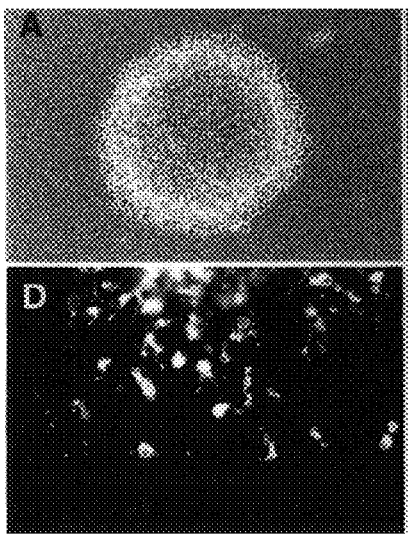
Figure 6B:
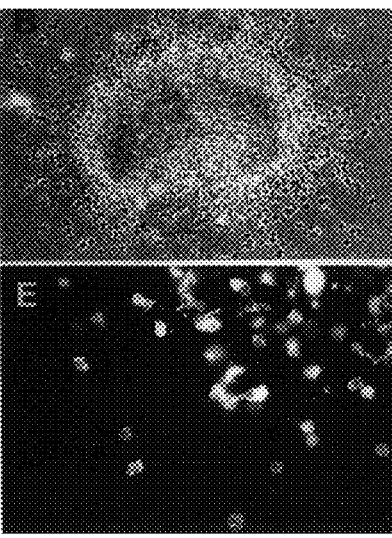
Figure 6C:
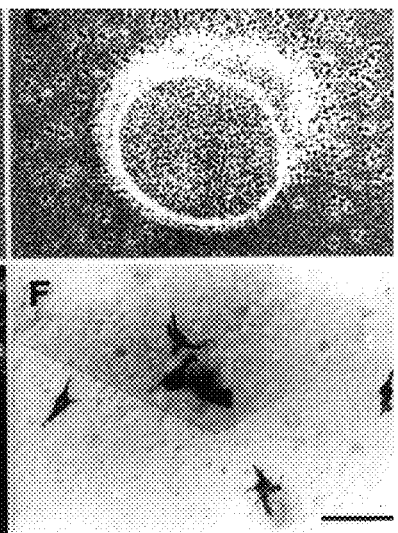
Figure 6D:
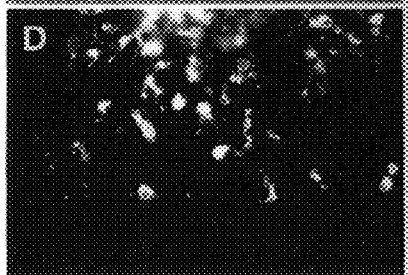
Figure 6E:
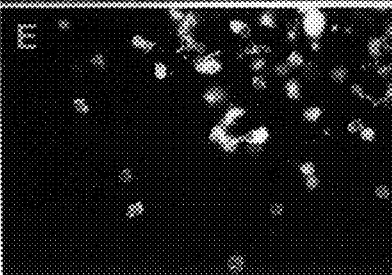
Figure 6F:
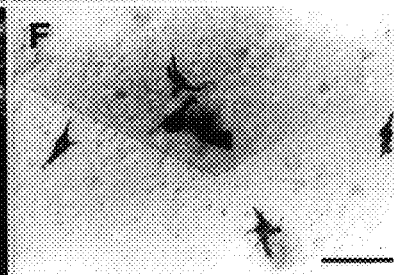

To examine whether dsl-1 might regulate the differentiation or migration of neural crest cells, the intermediate ([i]) region of the neural plate was isolated from stage 10 embryos and grown as explants in vitro (Yamada et al. 1993). As described (Yamada et al. 1993) few cells migrated from [i]-neural plate explants grown in isolation for 48 h (FIGS. 6A,G). Addition of dsl-1$^{myc}$ ($3\times10^{-11}$M) for 48 h resulted in a 15-fold increase in the number of cells that migrated from [i]-neural plate explants (FIGS. 6B,G). To examine whether these migratory cells share surface properties with chick neural crest cells, cultures grown for 48 h in the presence of dsl-1$^{myc}$ were labeled with monoclonal antibodies directed against HNK-1, the 81 integrin subunit and chick p75. Over 90% of cells that had migrated from the [i]-neural plate explants in the presence of dsl-1$^{myc}$ expressed HNK-1 and β1 integrin on their surface (FIG. 6D,E) and about 30% expressed p75 (not shown). These results show that cells induced to migrate from [i]-neural plate explants have the properties of neural crest cells.

To determine whether the cells that are induced to migrate from [i]-neural plate explants by dsl-1 can differentiate into cell types known to derive from the neural crest, the generation of melanocytes, which can be identified unambiguously in vitro by the presence of lemanin pigmentation was studied. In these experiments we used [i]-neural plate explants from quail embryos which exhibit properties in vitro similar to those of equivalently staged [i]-neural plate explants from the non-pigmented chick strain used for all other experiments were used (not shown). Melanocyte differentiation from neural crest cells in vitro has been shown to require permissive factors that can be provided in the form of chick embryo extract (CEE) or serum (Baroffio et al. 1988; Maxwell et al. 1988). [i]-Neural plate explants were therefore grown in dsl-1$^{myc}$ ($3\times10^{-11}$M) for 48 h to promote the migration of cells, after which dsl-1$^{myc}$ was removed and the medium supplemented with 10% CEE and 10% fetal calf serum and grown for a further 72 h. Under these conditions, 10–15% of the cells that had emigrated from [i]-neural plate explants expressed melanin pigment and exhibited dendritic morphology (FIG. 6F) indicating the presence of melanocytes. Control experiments showed that addition of CEE and serum after exposure of [i]-neural plate explants to dsl-1$^{myc}$ for 48 h did not increase further the number of migratory cells (not shown). Moreover, melanocytes were not observed when [i]-neural plate explants were exposed to medium containing CEE and serum for 72 h in the absence of dsl-1$^{myc}$ (not shown). These results indicate that cells induced to migrate from [i]-neural plate explants by dsl-1$^{myc}$ can differentiate into at least one cell type known to derive from the neural crest.

In contrast to neural crest cells that derive from the dorsal neural tube [i]-neural plate explants (Yamada et al. 1993), cells that had been induced to migrate from [i]-neural plate explants by dsl-1$^{myc}$ did not express neuronal markers or exhibit neuronal morphology when examined after 48 h (not shown). This result suggests that dsl-1 can promote the initial differentiation of neural crest cells from neural plate cells, but that dsl-1 alone does not support the subsequent differentiation of these cells into neurons.

Figure 6G:
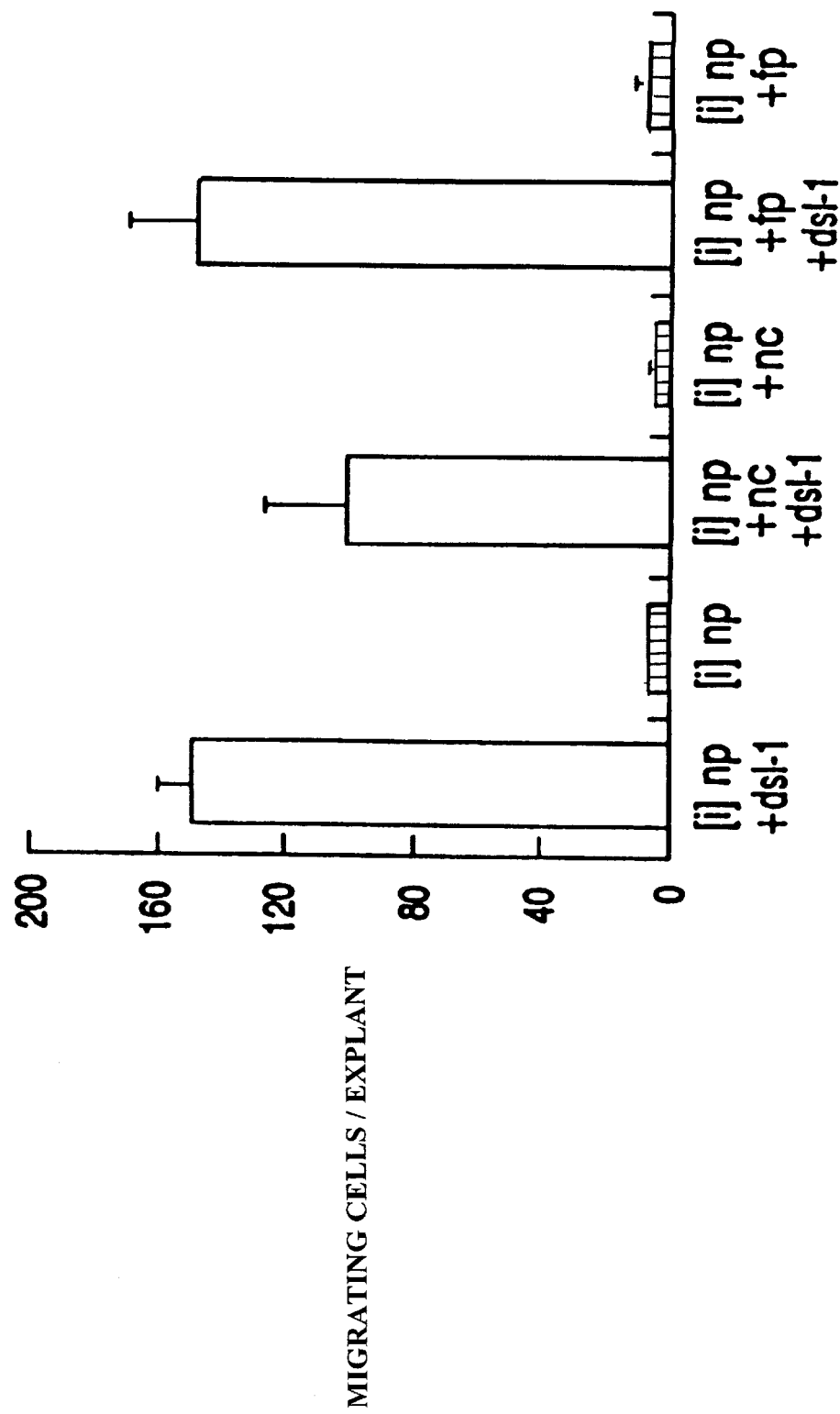

The presence of migratory neural crest-like cells was also monitored to address the fate of cells in [i]-neural plate explants that have been exposed both to ventralizing signals and to dsl-1$^{myc}$. [i]-Neural plate explants grown in contact with the notochord or floor plate for 48 h in the presence of dsl-1myc($3\times10^{-11}$M) exhibited a 12–15 fold increase in the number of migratory cells, similar to that observed when isolated [i]-neural plate explants were exposed to dsl-1$^{myc}$ (FIG. 6G). These cells also expressed HNK-1, β1 integrin and p75 on their surface (not shown). These findings suggest that dsl-1$^{myc}$ promotes the initial differentiation of neural crest cells in the presence of ventralizing signals from the notochord and floor plate.

At present, the lack of selective markers has forbidden studies of whether dsl-1 promotes the differentiation of other neural cell types that derive from the dorsal neural tube.

Regulation of Motor Neuron Differentiation

To examine whether dsl-1 also influences the differentiation of ventral cell types, expression of the LIM homeodomain protein Islet-1 (Karlson et al 1990; Ericson et al. 1992), which provides a marker for the induction of motor neurons in [i]-neural plate explants in response to diffusible signal from the notochord or floor plate was monitored (Yamada et al., 1993).

Figure 7A:
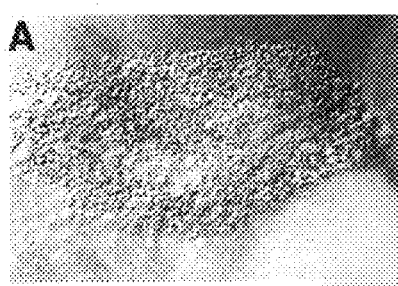
Figure 7B:
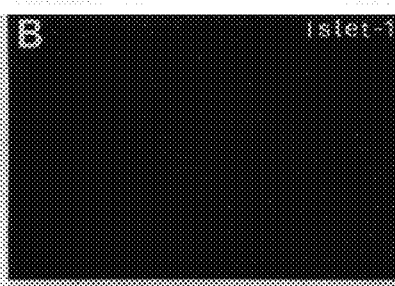
Figure 7C:
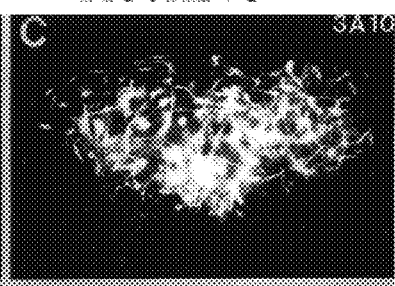
Figure 7D:
Figure 7E:
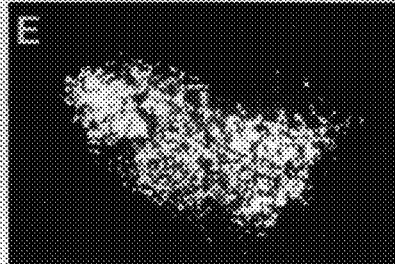
Figure 7F:
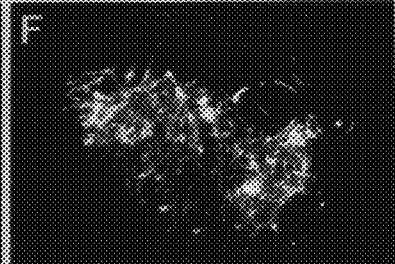
Figure 8B:
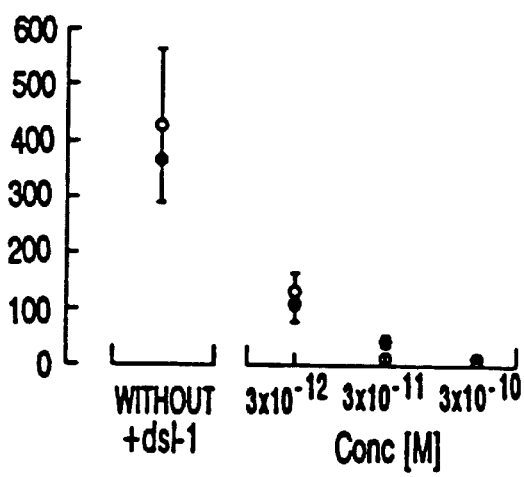

[i]-Neural plate explants grown in vitro for 48 h contained few (usually <5) Islet-1+ cells (FIGS. 7A,B;8A,C). In contrast, [i]-neural plate explants grown in contact with notochord or floor plate exhibited a 50–100-fold increase in Isl-1+ cells (FIGS. 7D,E;8A). Addition of dsl-1$^{myc}$ to recombinates of [i]-neural plate with notochord or floor plate produced a concentration-dependent decrease in the number of Islet-1+ cells present in explants (FIGS. 7J,K;8A,B). At concentrations of dsl-1$^{myc}$ of $3\times10^{-11}$M or greater, the differentiation of Islet-1+ cells was suppressed by over 95% (FIG. 8B). Dsl-1$^{myc}$ also abolished the expression of SC1 from regions of the [i]-neural plate explant distant from the junction with the inducing tissue (not shown) suggesting that dsl-1$^{myc}$ suppresses motor neuron properties other than Isl-1. Addition of dsl-1$^{myc}$ to neural plate explants grown alone did not induce Islet-1+ cells (not shown).

A truncated dsl-1 cDNA in cos-7 cells was expressed and compared its activity with that of native dsl-1 or dsl-1$^{myc}$ to control for the presence of cos-7 cell-derived inhibitory contaminants in preparation of affinity-purified dsl-1$^{myc}$. The induction of Islet-1+ cells by floor plate was suppressed over 95% by a 1:1000 dilution of conditioned medium from cos-7 cells transfected either with unmodified dsl-1 or with dsl-$^{myc}$ cDNAs (not shown). In contrast, medium derived from cos-7 cells expressing the truncated dsl-1 CDNA did not significantly reduce the number of Islet-1+ cells induced by floor plate (364±62 cells in the absence and 287±45 cell in the presence of medium containing truncated dsl-1, mean ±s.e.m., n=4, p>0.10).

Figure 8C:
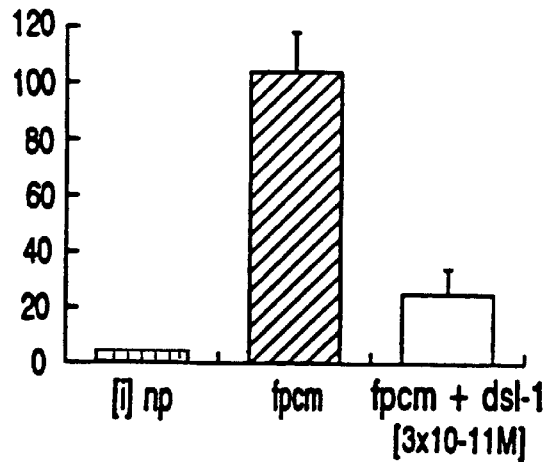

Dsl-1 could inhibit the generation of Islet-1+ cells by preventing [i]-neural plate cells from responding to inductive signals or by inhibiting the production of this signal by the notochord and floor plate. The effects of dsl-1$^{myc}$ on Islet-1+ cells in [i]-neural plate explants exposed to floor plate-conditioned medium were examined to distinguish these possibilities (Yamada et al. 1993). A 1:10 dilution of floor plate-conditioned medium produced a ~30 fold increase in the number of Isl-1+ cells (FIGS. 7G,H;8C). Addition of both dsl-1$^{myc}$ and floor plate-conditioned medium to neural plate explants grown alone resulted in a 76% decrease in the number of Islet-1+ cells (FIG. 8C). This result indicates that the inhibition of Islet-1+ cells results, at least in part, from a direct action of dsl-1 on [i]-neural plate cells.

To examine whether the suppression of Islet-1+ cells is accompanied by a more general inhibition of neuronal differentiation, explants processed for Islet-1 expression were double-labelled with MAb 3A10, a general neuronal marker (Furley et al., 1990). Although the labelling of both cell bodies and axons by 3A10 made it difficult to count the number of neurons accurately, there was no obvious difference in the number of 3A10+cells in [i]-neural plate explants exposed to concentrations of dsl-1$^{myc}$ that almost completely suppressed the differentiation of Islet-1+ cells (Compare FIGS. 7I and 7L). These results show that extensive neuronal differentiation still occur under conditions in which the induction of Islet-1+ cells is suppressed.

Experimental Discussion

Dorsoventral patterning within the neural tube appear to begin at the neural plate stage and to involve the action of both contact-mediated and diffusible inductive signals that derive initially from the notochord and later from the floor plate. A contact-mediated signal appears to be required for floor plate differentiation whereas motor neuron differentiation can be induced by diffusible factors (Placzek et al. 1993; Yamada et al. 1993). The specification of dorsal cell types may, however, require different factors since dorsal cell types persist in the spinal cord of embryos in which the notochord and floor plate have been eliminated.

To begin to define factors involved in specifying the fate of cells in the dorsal neural tube, a novel member of the TGFB gene family, dorsalin-1 (dsl), the expression of which is restricted to the dorsal neural tube was cloned and characterized. The dorsal restriction in expression of dsl-1 appears to be established by signals from the notochord which act on overlying neural plate cells prior to the onset of dsl-1 transcription to prevent ventral expression of the gene after closure of the neural tube (FIG. 9A). The persistence of dsl-1 mRNA expression in the absence of the notochord and floor plate provides evidence that the expression of genes that are restricted to the dorsal neural tube is independent of ventralizing signals. Dorsal cell fates may be specified by the exposure of neural plate cells to early dorsalizing signals, perhaps from adjacent non-neural ectoderm (Takahashi et al. 1992) which induce the potential to express dsl-1 and other dorsal genes.

Once the dorsal expression of dsl-1 is established, dsl-1 protein could function in several different ways to control cell differentiation in the neural tube. First, dsl-1 may promote the differentiation of cell types that derive from the dorsal neural tube (FIG. 9Bi). Second, the expression of dsl-1 could ensure that the dorsal neural tube is refractory to ventralizing signals from the notochord (FIG. 9Bii). Finally, dsl-1 protein could diffuse and influence the fate of cells in more ventral regions of the neural tube (FIG. 9ABiii). The interactions of dsl-1 and other factors from the dorsal neural tube with ventralizing signals from the ventral midline could, therefore control the identity of cell types and the position at which they are generated along the entire dorsoventral axis of the neural tube.

Dsl-1 May Promote Neural Crest Cell Differentiation

One function of dsl-1 suggested by the pattern of expression of dsl-1 mRNA could be to promote the differentiation of cell types that are generated in the dorsal neural tube. Neural crest cells constitute one of the major cell types that derive from precursors located in the dorsal neural tube. The present in vitro studies provide evidence that dsl-1 promotes the initial differentiation of cells with neural crest-like properties from [i]-neural plate explants, but that cells exposed to dsl-1 alone appear unable to progress to fully differentiated cell types such as neurons or melanocytes. One possible reason for this is that dsl-1 itself may inhibit neural crest cells from further differentiation. In support of this, TGFB 1 has been shown to inhibit the differentiation of neural crest cells into melanocytes (Stocker et al. 1991; Rogers et al. 1992) and to promote the production of extracellular matrix components such as fibronectin (Rogers et al. 1992) that can inhibit neuronal differentiation (Stemple and Anderson, 1992). Alternatively other dorsally-restricted factors that are absent from [i]-neural plate explants may be required for the progression of neural crest cell differentiation.

TGFβ 1 has also been shown to accelerate the migration of neural crest cells from premigratory regions of the neural tube (Delannet and Duband, 1992). The action of dsl-1 to promote the migration of neural crest-like cells from [i]-neural plate explants differs from this effect in that cells in these explants do not give rise to neural crest cells in the absence of dsl-1 even when maintained in vitro for 96 h (Yamada, unpublished observations). Nevertheless, dsl-1 may mimic the ability of TGFβ 1 to accelerate neural crest migration and could therefore be involved both in specifying the fate of premigratory neural crest precursors and in inducing the migration of these cells from the dorsal neural tube.

It remains unclear whether the differentiation of other classes of dorsal neurons is regulated by dsl-1. Neurons with the properties of dorsal commissural neurons can differentiate in rat neural plate explants grown in isolation (Placzek et al. 1993). Thus it is possible that some dorsal cell types can differentiate independently of dsl-1. Alternatively, neural plate explants grown in vitro may begin to express dsl-1 at levels sufficient to drive the differentiation of some but not all dorsal cell types.

Dsl-1 as an Inhibitor of Ventral Cell Type Differentiation

Dsl-1 suppresses the differentiation of motor neurons in [1]-neural plate explants exposed to ventralizing signals from the notochord or floor plate. This finding raises the possibility that dsl-1 interacts with ventralizing signals to control cell fate along the dorsoventral axis of the neural tube. Although, dsl-1 expression occurs after signals from the notochord and floor plate have begun to specify ventral cell fates (Yamada et al. 1993), its expression precedes the overt differentiation of motor neurons and other ventral neurons (Ericson et al. 1992). Indeed, the first marker of motor neuron differentiation, Islet-1, is not expressed until stage 15 (Ericson et al. 1992), or about 18–20 h after neural tube closure and the onset of dsl-1 expression. Thus, in the period between the initial specification and overt differentiation of neurons, dsl-1 may accumulate to levels that are sufficient to influence neuronal differentiation.

The ability of dsl-1 to inhibit motor neuron differentiation could be involved in preventing the generation of motor neurons and other ventral cell types in the dorsal neural tube. This presupposes that ventralizing signals from the notochord and floor plate can influence dorsal regions of the neural tube. Secreted factors from the floor plate have been shown to diffuse over long distances through the neuroepithelium (Placzek et al. 1990). Moreover the position of the ventral boundary of the domain of dsl-1 expression suggests that signals from the notochord can influence at least two third of the neural tube. Thus, expression of dsl-1 within the dorsal third of the neural tube could make cells in this region refractory to long range ventralizing signals from the notochord and floor plate.

The potential contributions of dsl-1 to cell differentiation along the dorso-ventral axis of the neural tube will also depend on the range of action of dsl-1 itself. Since dsl-1 is readily secreted from cells in vitro, dsl-1 may diffuse ventrally, beyond the domain of dsl-1 mRNA expression, to influence the response of cells in intermediate regions of the neural tube. Again, the ability of dsl-1 to antagonize the response of neural cells to ventralizing signals from the notochord and floor plate could be relevant both to the differentiation of motor neurons and to other ventral cell types.

Prevention of Dsl-1 Expression Ventrally May be Required for Ventral Cell Type Differentiation Dsl-1 promotes neural crest cell migration and inhibits motor neuron differentiation in the presence of the notochord or floor plate. These findings suggest that the actions of dsl-1 dominate over ventralizing signals. Thus, the inhibition of dsl-1 expression from ventral regions of the neural tube that is achieved by early signals from the notochord may be necessary for the differentiation of ventral cell types. The absence of ventral cell types in the neural tube of embryos lacking a notochord could, therefore, result either from a ventral expansion in the domain of dsl-1 expression or from the loss of ventralizing signals. However, in such operated embryos the neural tube is reduced in size (van Straaten and Hekking, 1991), thus, the death (Homma and Oppenheim, 1992) or arrested division (Placzek et al. 1993) of ventral cells could also contribute to the presence of dorsal cell types in regions of the neural tube that appear to be ventral.

Dsl-1 and the TGFβ Family

In addition to dsl-1, several other members of the BMP (DVR) subfamily of TGFβ-like genes are expressed in the embryonic nervous system. Other BMP-like proteins may therefore mimic the actions of dsl-1 on neural cell differentiation. In preliminary studies, the induction of motor neurons was found to be also suppressed by cos-7 cell-derived BMP-4 (Basler et al. unpublished). In the spinal cord and hindbrain, the BMP-4 (DVR-4) gene is expressed selectively by cells in the roof plate whereas in the diencephalon, the gene is found at the ventral midline (Jones et al., 1991). The expression of BMP-4 in the ventral diencephalon coincides with, and could perhaps contribute to the absence of motor neurons from the embryonic forebrain. The embryonic distribution of most other BMP genes is not known although Vgr-1 (BMP-6/DVR-6) is expressed by cells immediately adjacent to the floor plate in the spinal cord (Jones et al., 1991) and GDF-1 appears to be expressed widely throughout the embryonic nervous system (Lee, 1990, 1991). Studies to determine whether widely distributed proteins such as GDF-1 mimic the actions of dsl-1 will be important in evaluating the role of this gene family in neural patterning.

The involvement of dsl-1 in the control of cell differentiation along the dorsoventral axis of the neural tube extends the range of activities described for members of the TGFB family during embryonic development. Studies in Xenopus embryos have provided evidence that activin can control the identity of mesodermal cell types in a concentration-dependent manner (Ruiz i Altaba and Melton, 1989; Green et al. 1992). In addition, the pattern of expression and possible functions of dsl-1 in the neural tube has parallels with that of the decapentaplegic gene (dpp) in Drosophila embryonic development (Ferguson and Anderson, 1992a,b). Dorsoventral patterning in the early Drosophila embryo involves a dorsal restriction of dpp expression (St. Johnston and Gelbart, 1987) that is achieved by ventral-midline derived signals that inhibit dpp expression ventrally (Ray et al. 1991). Genetic inactivation of this ventral signalling pathway or introduction of dpp activity ventrally, changes the fate of cells along the dorsoventral axis of the embryo (Ferguson and Anderson, 1992b). In the neural tube, the dorsal restriction of dsl-1 mRNA by early signals from the notochord could generate a gradient of dsl-1 activity along the dorsoventral axis of the neural tube. Alone, or in conjunction with ventralizing signals from the notochord and floor plate, a gradient of dsl-1 could influence the fate of cells according to their dorsoventral position within the neural tube.

REFERENCES

Abo, T. and Balch, C. M. (1981) A differentitation antigen of human NK and K cells identified by a monoclonal antibody (HNK-1) J.Immun. 127:1024–1029.

Barr, P. J. (1991) Mammalian subtilisins: The long-sought after dibasic processing endoproteases. Cell 66:1–3.

Baroffio, A., Dupin, E. and LeDouarin, N. M. (1988) Clone-forming ability and differentiation potential of migratory neural crest cells. Proc. Natl. Acad. Sci. 85:5325–5329.

Bernd, P. (1985) Appearance of nerve growth factor receptors on cultured neural crest cell. Devl. Biol. 112:145–156.

Bronner, Fraser, M. and Fraser, S. (1988) Cell lineage analysis shows multipotentiality of some avian neural crest cells. Nature 335:161–164.

Celeste, A. J., Iannazzi, J. A., Taylor, R. C., Hewick, R. M., Rosen, V., Wang, E. A. and Wozney, J. M. (1990) Identification of transforming growth factor β family members present in bone-inductive protein purified from bovine bone. Proc. Natl. Acad. Sci. 87:9843–9847.

Daopin, S., Piez, K. A., Ogawa, Y. and Davies, D. R. (1992) Crystal structure of transforming growth factor-β2: An unusual fold for the superfamily. Science 257:369–373.

Darnell, D. K., Schoenwold, G. C. and Ordahl, C. P. (1992) Changes in dorsoventral but not rostrocaudal regionalization of the chick neural tube in the absence of cranial notochord, as revealed by expression of engrailed-2. Dev. Dyn. 193:389–396.

Delannet, M. and Duband, J-L. (1992) Transforming growth factor-B control of cell-substratum adhesion during avian neural crest cell emigration in vitro. Dev. 116:275–287.

Devereux, J., Haeberli, P. and Smithies, O. (1984) A comprehensive set of sequence analysis programs for the VAX. Nucl. Acid Res 12:387–395.

Dodd, J., Morton, S. B., Karagoegeos, D., Yamamoto, M., and Jessell, T. M. (1988) Spatial regulation of axonal glycoprotein expression on subsets of embryonic spinal neurons. Neuron 1:105–116.

Ericson, J., Thor, S., Edlund, T., Jessell, T. M. and Yamada, T. (1992) Early stages of motor neuron differentiation revealed by expression of homeobox gene Islet-1. Science 256:1555–1560.

Evan, G. I., Lewis, G. K., Ramsay, G. and Bishop, J. M. (1985) Isolation of monoclonal antibodies specific for humanc-myc protooncogene product. Mol. Cell Biol. 5:3610–3616.

Ferguson, E. L. and Anderson, K. V. (1992a) Localized enhancement and repression of the activity of the TGF-β family member, decapentaplegic, is necessary for dorsal-ventral pattern formation in the Drosophila embryo. Development 114:583,597.

Ferguson, E. L. and Anderson, K. V. (1992b) Decapentaplegic acts as a morphogen to organize dorsal-ventral pattern in the Drosophila embryo. Cell 71:451–461.

Furley, A. J., Morton, S. B., Manalo, D., Karagogeos, D., Dodd, J. and Jessell, T. M. (1990) The axonal glycoprotein TAG-1 is an immunoglobulin superfamily member with neurite outgrowth-promoting activity. Cell 61:157–170.

Grabowski, C. T. (1956) The effects of the excision of Hensen's Node on the early development of the chick embryo. J.Exp.Zool. 133:301–343.

Green, J. B. and Smith, J. C. (1990) Graded changes in dose of a Xenopus activin A homologue elicit stepwise transitions in embryonic cell fate. Nature 347:391–394.

Green, J. B., New, H. V. and Smith, J. C. (1992) Responses of embryonic xenopus cells to activin and FGF are separated by multiple dose thresholds and correspond to distinct axes of the mesoderm. Cell 71:731–739.

Greve, J. M. and Gottlieb, D. I. (1982) Monoclonal antibodies which alter the morphology of cultured chick myogenic cells. J.Cell. Biochem. 18:221–229.

Hamburger, V. and Hamilton, H. (1951) A series of normal stages in the development of chick embryo. J.Morph. 88:49–92.

Harland, R. M. (1991) In situ hybridization: an improved whole mount method for Xenopus embryos. Meth.Enxymol. 36:675–685.

Hatta, K., Kimmel, C. B., Ho, R. K. and Walker, C. (1991) The cyclops mutation blocks specification of the floor plate of the zebrafish central nervous system. Nature 350:339–341.

Hirano, S., Fuse, S. and Sohal, G. S. (1991) The effect of the floor plate of pattern and polarity in the developing central nervous system. Science 251:310–313.

Hoffman, F. M. (1991) Transforming growth factor-β-related genes in Drosophila and vertebrate development. Current Opinion in Cell Biology 3:947–952.

Homma, S. and Oppenheim, R. W. (1992) Notochord dependent cell survival in the ventral half of the chick neural tube. Soc. Neurosc.Abst. 43.

Jones, C. M., Lyons, K. M. and Hogan, B. L. M. (1991) Involvement of bone morphogenetic protein-4 (BMP-4) and vgr-1 in morphogenesis and neurogenesis in the mouse. Development 111:531–542.

Karlsson, O., Thor, S., Norbert, T., Ohlsson, H., and Edlund, T. (1990) Insulin gene enhancer binding protein Isl-1 is a member of a novel class of proteins containing both a homeo- and a Cys-His domain. Nature 344:879–882.

Klar, A., Baldassare, M. and Jessell, T. M. (1992) F-spondin: A gene expressed at high levels in the floor plate encodes a secreted protein that promotes neural cell adhesion and neurite extension. Cell 69:95–110.

Lee, S. J. (1990 Identification of a novel member (GDF-1) of the transforming growth factor-b superfamily. Molecular Endocrinology 4:1034–1040.

Lee, S. J. (1991) Expression of growth/differentiation factor 1 in the nervous system: Conservation of a bicistronic structure. Proc.Natl.Acad.Sci. 88:4250–4254.

Lyons, K. M., Jones, C. M. and Hogan, B. L. M. (1991) The DVR gene family in embryonic development. Trends Genet. 7:408–412.

Maxwell, G. D., Forbes, M. E. and Christie, D. S. (1988) Analysis of the development of cellular subsets present in the neural crest using cell sorting and cell culture. Neuron 1:557–568.

Placzek, M., Tessier-Lavigne, M., Yamada, T., Jessell, T. M. and Dodd, J. (1990a). Mesodermal control of neural cell identity: floor plate induction by the notochord. Science 250:985–988.

Placzek, M., Tessier-Lavigne, M., Jessell, T. M. and Dodd, J. (1990b) Orientation of commissural axons in vitro in response to a floor plate-derived chemoattractant. Development 110:19–30.

Placzek, M., Yamada, T., Tessier-Lavigne, M., Jessell, T. M. and Dodd, J. (1991) Control of dorso-ventral pattern in vertebrate neural development: induction and polarizing properties of the floor plate. Development.Suppl. 2:105–122.

Placzek, M., Jessell, T. M. and Dodd, J. (1993) Induction of floor plate differentiation by contact-dependent, homeogenetic signals. Development 117 (In Press).

Ray, R. P., Arora, K., Nusslein-Volhard, C. and Gelbart, W. M. (1991) The control of cell fate along the dorsal-ventral axis of the Drosophila embryo. Development 113:35–54.

Rogers, S. L., Gegick, P. J., Alexander, S. M. and McGuire, P. G. (1992) Transforming growth factor-β alters differentiation in cultures of avian neural crest-derived cells: effects on cell morphology, proliferation, fibronectin expression and melanogenesis. Dev. Biol. 151:192–203.

Ruizi Altaba, A. and Melton, D. A. (1989) Interaction between peptide growth factors and homeobox genes in the establishment of anteriro-posterior polarity in frog embryos. Nature 341:33–38.

Sanger, F., Nicklen, S. and Coulson, A. R. (1977). DNA sequencing with chain-terminating inhibitors. Proc.Natl.Acad.Sci.USA 74:5463–5467.

Schlunegger, M. P. and Grutter, M. G. (1992) An unusual feature revealed by the crystal structure of 2.2A resolution of human transforming growth factor-β2. Nature 358:430.

Sieber-Blum, M. and Cohen, A. M. (1980) Clonal analysis of quail neural crest cells: They are pluripotent and differentiate in vitro in the absence of non-crest cells Devl. Biol. 80:96–106.

Smith, T. F. and Waterman, M. S. (1981) Identification of common molecular subsequences. J. of Mol. Biol. 147:195–197.

Smith, J. L. and Schoenwolf, G. C. (1989) Notochordal induction of cell wedging in the chick neural plate and its role in neural tube formation. J. Exp. Zool. 250:49–62.

Smith-Thomas, L. C. and Fawcett, J. W. (1989) Expression of Schwann cell markers by mammalian neural crest cells. Development 105:251–262.

Stemple, D. L. and Anderson, D. J. (1992) Isolation of a Stem Cell For Neurons and Glia from the Mammalian Neural Crest. Cell 71:973–985.

St. Johnson, R. D. and Gelbart, W. M. (1987) Decapentaplegic transcripts are localized along the dorsal-ventral axis of the Drosophila embryo. The EMBO Journal 6:2785–2791.

Stocker, K. M., Sherman, L., Rees, S. and Ciment, G. (1991) Basic FGF and TGF-β1 influence commitment to melanogenesis in neural crest-derived cells of avian embryos. Dev. 111:635–645.

Takahashi, Y., Monsoro-Burq, A-H., Bontoux, M. and Le Douarin, N. M. (1992) A role for Quox-8 in the establishment of the dorsoventral pattern during vertebrate development. Proc. Natl. Acad. Sci. 89:10237–10241.

Tanaka, H. and Obata, K. (1984) Developmental changes in unique cell surface antigens of chick embryo spinal motor neurons and ganglion cells. Devl. Biol. 106:26–37.

Tanaka, H., Agata, A. and Obata, K. (1984) A new membrane antigen revealed by monoclonal antibodies is associated with motoneuron axonal pathways. Dev. Biol. 132:419–435.

Tessier-Lavinge, M., Placzek, M., Lumsden, A. G. S., Dodd, J. and Jessell, T. M. (1988) Chemotropic guidance of developing axons in the mammalian central nervous system. Nature :336:775–778.

Thies, R. S., Bauduy, M., Ashton, B. A., Kurtzberg, L., Wozney, J. M. and Rosen, V. (1992) Recombinant human bone morphogenetic protein-1 induces osteoblastic differentiation in W-20-17 stromal cells. Endocrinology 130:1318–1324.

Thomsen, G., Woolf, T., Whitman, M., Sokol, S., Vaughan, J., Vale, W. and Melton, D. A. (1990) Activins are expressed early in Xenopus embryogenesis and can induce axial mesoderm and anterior structures. Cell 63:485–493.

Thor, S., Ericson, J., Brannstrom, T. and Edlund, T. (1991) The homeodomain LIM protein Isl-1 is expressed in subsets of neurons and endocrine cells in the adult rat. Neuron 7:881–889.

van Straaten, H. M. W., Hekking, J. W. M., Wiertz-Hoessels, E. L., Thors, F. and Drukker, J. (1988) Effect of the notochord on the differentiation of a floor plate area in the neural tube of the chick embryo. Anat. Embryol. 177:317–324.

van Straaten, H. M. W. and Hekking, J. W. M. (1991) Development of floor plate, neurons and axonal outgrowth pattern in the early spinal cord of the notochord-deficient chick embryo. Anat. Embryol. 184:55–63.

Wharton, K. A., Thomsen, G. H. and Gelbart, W. M. (1991) Drosophila 60A gene, another transforming growth factor 8 family member, is closely related to human bone morphogenetic proteins. Proc. Natl. Acad. Sci. 88:9214–9218.

Wilkinson, D. G., Bailes, J. A. and McMahon, A. P. (1987) Expression of the proto-oncogene int-1 is restricted to specific neural cells in the developing mouse embryo. Cell 58:79–88.

Wozney, J. M., Rosen, V., Celeste, A. J., Mitsock, L. M., Whitters, M. J., Driz, R. W., Hewick, R. M. and Wang, E. A. (1988) Novel regulators of bone formation: molecular clones and activities. Science 242:1528–1534.

Yamada, T., Placzek, M., Tanaka, H., Dodd, J. and Jessell, T. M. (1991) Control of cell pattern in the developing nervous system: polarizing activity of the floor plate and notochord. Cell 64:635–647.

Yamada, T., Pfaff, S., Edlund, T. and Jessell, T. M. (1993) Control of cell pattern in the neural tube: Motor neuron induction by diffusible factors from notochord and floor plate. Cell Submitted

What is claimed is:

1. An isolated nucleic acid comprising the nucleic acid sequence set forth in SEQ ID NO: 1, which nucleic acid encodes a dorsalin-1 polypeptide capable of promoting neural crest cell differentiation and inhibiting motor neuron differentiation.

2. The nucleic acid of claim 1 which is DNA.

3. The nucleic acid of claim 1 which is cDNA.

4. An isolated nucleic acid of claim 2 operatively linked to a promoter of RNA transcription.

5. A vector which comprises the isolated nucleic acid of claim 4.

6. The vector of claim 5, wherein the vector is a plasmid.

7. The vector of claim 6, wherein the plasmid is designated pKB502 (ATCC Accession No. 75321).

8. A host vector system for the production of a polypeptide, which host vector system comprises the vector of claim 5 in a suitable host cell.

9. The host vector system of claim 8, wherein the suitable host cell is a bacterial cell, insect cell, or animal cell.

10. A method of producing a polypeptide which comprises growing the host vector system of claim 8 under suitable conditions permitting production of the polypeptide and recovering the polypeptide so produced.

11. The nucleic acid of claim which is RNA.

12. An isolated nucleic acid which encodes a dorsalin-1 polypeptide, wherein the polypeptide comprises the sequence set forth in SEQ ID NO: 2.

13. An isolated nucleic acid which encodes a mouse dorsalin-1 polypeptide, wherein the polypeptide comprises the sequence set forth in SEQ ID NO: 9.

* * * * *

```
                       SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
        (A) LENGTH: 1603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO
```

(iv) ANTI-SENSE: NO (ix) FEATURE:
         (A) NAME/KEY: CDS
         (B) LOCATION: 91..1371

(xi) SEQUENCE DESCRIPTION: SEQ ID NO:1:

```
CCTTTCCTCT GTCTGTAAAG ATTCAACATT TTTAATCAGT TAAAATACTT TGTCCTCTTG        60

TCTCTCCATC AGAAAGTAAA TACATAAGAA ATG CAT TAT TTT GGA GTA TTA GCT        114
                                  Met His Tyr Phe Gly Val Leu Ala
                                    1               5

GCA CTG TCT GTT TTC AAT ATC ATT GCC TGC CTG ACA AGA GGC AAG CCT        162
Ala Leu Ser Val Phe Asn Ile Ile Ala Cys Leu Thr Arg Gly Lys Pro
     10                  15                  20

TTG GAA AAC TGG AAA AAG CTA CCA GTT ATG GAA GAG TCT GAT GCA TTC        210
Leu Glu Asn Trp Lys Lys Leu Pro Val Met Glu Glu Ser Asp Ala Phe
 25                  30                  35                  40

TTT CAT GAT CCT GGG GAA GTG GAA CAT GAC ACC CAC TTT GAC TTT AAA        258
Phe His Asp Pro Gly Glu Val Glu His Asp Thr His Phe Asp Phe Lys
                 45                  50                  55

TCT TTC TTG GAG AAT ATG AAG ACA GAT TTA CTA AGA AGT CTG AAT TTA        306
Ser Phe Leu Glu Asn Met Lys Thr Asp Leu Leu Arg Ser Leu Asn Leu
             60                  65                  70

TCA AGG GTC CCC TCA CAA GTG AAG ACC AAA GAA GAG CCA CCA CAG TTC        354
Ser Arg Val Pro Ser Gln Val Lys Thr Lys Glu Glu Pro Pro Gln Phe
         75                  80                  85

ATG ATT GAT TTA TAC AAC AGA TAT ACA GCG GAC AAG TCC TCC ATC CCT        402
Met Ile Asp Leu Tyr Asn Arg Tyr Thr Ala Asp Lys Ser Ser Ile Pro
     90                  95                 100

GCA TCC AAC ATC GTG AGG AGC TTC AGC ACT GAA GAT GTT GTT TCT TTA        450
Ala Ser Asn Ile Val Arg Ser Phe Ser Thr Glu Asp Val Val Ser Leu
105                 110                 115                 120

ATT TCA CCA GAA GAA CAC TCA TTT CAG AAA CAC ATC TTG CTC TTC AAC        498
Ile Ser Pro Glu Glu His Ser Phe Gln Lys His Ile Leu Leu Phe Asn
                125                 130                 135

ATC TCT ATT CCA CGA TAT GAG GAA GTC ACC AGA GCT GAA CTG AGA ATC        546
Ile Ser Ile Pro Arg Tyr Glu Glu Val Thr Arg Ala Glu Leu Arg Ile
            140                 145                 150

TTT ATC TCC TGT CAC AAG GAA GTT GGG TCT CCC TCC AGA CTG GAA GGC        594
Phe Ile Ser Cys His Lys Glu Val Gly Ser Pro Ser Arg Leu Glu Gly
        155                 160                 165

AAC ATG GTC ATT TAT GAT GTT CTA GAT GGA GAC CAT TGG GAA AAC AAA        642
Asn Met Val Ile Tyr Asp Val Leu Asp Gly Asp His Trp Glu Asn Lys
    170                 175                 180

GAA AGT ACC AAA TCT TTA CTT GTC TCT CAC AGT ATT CAG GAC TGT GGC        690
Glu Ser Thr Lys Ser Leu Leu Val Ser His Ser Ile Gln Asp Cys Gly
185                 190                 195                 200

TGG GAG ATG TTT GAG GTG TCC AGC GCT GTG AAA AGA TGG GTC AAG GCA        738
Trp Glu Met Phe Glu Val Ser Ser Ala Val Lys Arg Trp Val Lys Ala
                205                 210                 215

GAC AAG ATG AAG ACT AAA AAC AAG CTA GAG GTT GTT ATA GAG AGT AAG        786
Asp Lys Met Lys Thr Lys Asn Lys Leu Glu Val Val Ile Glu Ser Lys
            220                 225                 230

GAT CTG AGT GGT TTT CCT TGT GGG AAG CTG GAT ATT ACT GTT ACT CAT        834
Asp Leu Ser Gly Phe Pro Cys Gly Lys Leu Asp Ile Thr Val Thr His
        235                 240                 245

GAC ACT AAA AAT CTG CCC CTA TTA ATA GTG TTC TCC AAT GAT CGC AGC        882
Asp Thr Lys Asn Leu Pro Leu Leu Ile Val Phe Ser Asn Asp Arg Ser
    250                 255                 260
```

-continued

```
AAT GGG ACA AAA GAG ACC AAA GTG GAG CTC CGG GAG ATG ATT GTT CAT     930
Asn Gly Thr Lys Glu Thr Lys Val Glu Leu Arg Glu Met Ile Val His
265                 270                 275                 280

GAA CAA GAA AGT GTG CTA AAC AAA TTA GGA AAG AAC GAC TCT TCA TCT     978
Glu Gln Glu Ser Val Leu Asn Lys Leu Gly Lys Asn Asp Ser Ser Ser
                285                 290                 295

GAA GAA GAA CAG AGA GAA GAA AAA GCC ATT GCT AGG CCC CGT CAG CAT    1026
Glu Glu Glu Gln Arg Glu Glu Lys Ala Ile Ala Arg Pro Arg Gln His
            300                 305                 310

TCC TCC AGA AGC AAG AGA AGC ATA GGA GCA AAC CAC TGT CGG AGA ACG    1074
Ser Ser Arg Ser Lys Arg Ser Ile Gly Ala Asn His Cys Arg Arg Thr
        315                 320                 325

TCA CTC CAT GTG AAC TTT AAA GAA ATA GGT TGG GAT TCT TGG ATC ATT    1122
Ser Leu His Val Asn Phe Lys Glu Ile Gly Trp Asp Ser Trp Ile Ile
    330                 335                 340

GCA CCC AAA GAT TAT GAG GCT TTT GAG TGT AAA GGA GGT TGC TTC TTC    1170
Ala Pro Lys Asp Tyr Glu Ala Phe Glu Cys Lys Gly Gly Cys Phe Phe
345                 350                 355                 360

CCC CTC ACA GAT AAT GTT ACG CCA ACC AAA CAT GCT ATT GTC CAG ACT    1218
Pro Leu Thr Asp Asn Val Thr Pro Thr Lys His Ala Ile Val Gln Thr
                365                 370                 375

CTG GTG CAT CTC CAA AAC CCA AAG AAA GCT TCC AAG GCC TGT TGT GTT    1266
Leu Val His Leu Gln Asn Pro Lys Lys Ala Ser Lys Ala Cys Cys Val
            380                 385                 390

CCA ACT AAA TTG GAT GCA ATC TCT ATT CTT TAT AAG GAT GAT GCT GGT    1314
Pro Thr Lys Leu Asp Ala Ile Ser Ile Leu Tyr Lys Asp Asp Ala Gly
        395                 400                 405

GTG CCC ACT TTG ATA TAT AAC TAT GAA GGG ATG AAA GTG GCA GAA TGT    1362
Val Pro Thr Leu Ile Tyr Asn Tyr Glu Gly Met Lys Val Ala Glu Cys
    410                 415                 420

GGC TGC AGG TAGTATATGC TGAATATCTA AGAATATACT CTTTTCTGCT            1411
Gly Cys Arg
425

GTCTGTGAAA CTGTACATTA GTGATGCAAA TGAAATCCT TGCAAACAAG GTTTGGAGCA  1471

CGGCATGGGG CTGGTTGTTG TTGCTGCTTT TAAAGGAAAG ATGGCATTTA AGAATGGCA  1531

ATCACTGTAA ATACCCTGCA TTATATACCA TTAATTAAAA CTTTGTGAGA TTGAAAAAAA 1591

AAAAAAAAAA AA                                                    1603

(2) INFORMATION FOR SEQ ID NO:2:

(i) SEQUENCE CHARACTERISTICS:
        (A) LENGTH: 427 amino acids
        (B) TYPE: amino acid
        (D) TOPOLOGY: linear (ii) MOLECULE TYPE: protein (xi) SEQUENCE DESCRIPTION: SEQ ID NO:2:

Met His Tyr Phe Gly Val Leu Ala Ala Leu Ser Val Phe Asn Ile Ile
1               5                   10                  15

Ala Cys Leu Thr Arg Gly Lys Pro Leu Glu Asn Trp Lys Lys Leu Pro
                20                  25                  30

Val Met Glu Glu Ser Asp Ala Phe Phe His Asp Pro Gly Glu Val Glu
            35                  40                  45

His Asp Thr His Phe Asp Phe Lys Ser Phe Leu Glu Asn Met Lys Thr
        50                  55                  60

Asp Leu Leu Arg Ser Leu Asn Leu Ser Arg Val Pro Ser Gln Val Lys
65                  70                  75                  80
```

```
Thr Lys Glu Glu Pro Pro Gln Phe Met Ile Asp Leu Tyr Asn Arg Tyr
                 85                  90                  95

Thr Ala Asp Lys Ser Ser Ile Pro Ala Ser Asn Ile Val Arg Ser Phe
                100                 105                 110

Ser Thr Glu Asp Val Val Ser Leu Ile Ser Pro Glu His Ser Phe
            115                 120                 125

Gln Lys His Ile Leu Leu Phe Asn Ile Ser Ile Pro Arg Tyr Glu Glu
            130                 135                 140

Val Thr Arg Ala Glu Leu Arg Ile Phe Ile Ser Cys His Lys Glu Val
145                 150                 155                 160

Gly Ser Pro Ser Arg Leu Glu Gly Asn Met Val Ile Tyr Asp Val Leu
                165                 170                 175

Asp Gly Asp His Trp Glu Asn Lys Glu Ser Thr Lys Ser Leu Leu Val
            180                 185                 190

Ser His Ser Ile Gln Asp Cys Gly Trp Glu Met Phe Glu Val Ser Ser
            195                 200                 205

Ala Val Lys Arg Trp Val Lys Ala Asp Lys Met Lys Thr Lys Asn Lys
            210                 215                 220

Leu Glu Val Val Ile Glu Ser Lys Asp Leu Ser Gly Phe Pro Cys Gly
225                 230                 235                 240

Lys Leu Asp Ile Thr Val Thr His Asp Thr Lys Asn Leu Pro Leu Leu
                245                 250                 255

Ile Val Phe Ser Asn Asp Arg Ser Asn Gly Thr Lys Glu Thr Lys Val
                260                 265                 270

Glu Leu Arg Glu Met Ile Val His Glu Gln Glu Ser Val Leu Asn Lys
            275                 280                 285

Leu Gly Lys Asn Asp Ser Ser Ser Glu Glu Glu Gln Arg Glu Glu Lys
            290                 295                 300

Ala Ile Ala Arg Pro Arg Gln His Ser Ser Arg Ser Lys Arg Ser Ile
305                 310                 315                 320

Gly Ala Asn His Cys Arg Arg Thr Ser Leu His Val Asn Phe Lys Glu
                325                 330                 335

Ile Gly Trp Asp Ser Trp Ile Ile Ala Pro Lys Asp Tyr Glu Ala Phe
                340                 345                 350

Glu Cys Lys Gly Gly Cys Phe Phe Pro Leu Thr Asp Asn Val Thr Pro
            355                 360                 365

Thr Lys His Ala Ile Val Gln Thr Leu Val His Leu Gln Asn Pro Lys
            370                 375                 380

Lys Ala Ser Lys Ala Cys Cys Val Pro Thr Lys Leu Asp Ala Ile Ser
385                 390                 395                 400

Ile Leu Tyr Lys Asp Asp Ala Gly Val Pro Thr Leu Ile Tyr Asn Tyr
                405                 410                 415

Glu Gly Met Lys Val Ala Glu Cys Gly Cys Arg
                420                 425

(2) INFORMATION FOR SEQ ID NO:3:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: protein (iii) HYPOTHETICAL: NO
```

-continued (iv) ANTI-SENSE: NO (xi) SEQUENCE DESCRIPTION: SEQ ID NO:3:

```
Glu His Ser Trp Ser Gln Ile Arg Pro Leu Leu Val Thr Phe Gly His
 1               5                  10                  15

Asp Gly Lys Gly His Pro Leu His Lys Arg Glu Lys Arg Gln Ala Lys
            20                  25                  30

His Lys Gln Arg Lys Arg Leu Lys Ser Ser Cys Lys Arg His Pro Leu
        35                  40                  45

Tyr Val Asp Phe Ser Asp Val Gly Trp Asn Asp Trp Ile Val Ala Pro
     50                  55                  60

Pro Gly Tyr His Ala Phe Tyr Cys His Gly Glu Cys Pro Phe Pro Leu
 65                  70                  75                  80

Ala Asp His Leu Asn Ser Thr Asn His Ala Ile Val Gln Thr Leu Val
                85                  90                  95

Asn Ser Val Asn Ser Lys Ile Pro Lys Ala Cys Cys Val Pro Thr Glu
                100                 105                 110

Leu Ser Ala Ile Ser Met Leu Tyr Leu Asp Glu Asn Glu Lys Val Val
            115                 120                 125

Leu Lys Asn Tyr Gln Asp Met Val Val Glu Gly Cys Gly Cys Arg
        130                 135                 140
```

(2) INFORMATION FOR SEQ ID NO:4:

(i) SEQUENCE CHARACTERISTICS:
       (A) LENGTH: 144 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

```
Asp Asp Gly Arg His Lys Ala Arg Ser Ile Arg Asp Val Ser Gly Gly
 1               5                  10                  15

Glu Gly Gly Gly Lys Gly Gly Arg Asn Lys Arg His Ala Arg Arg Pro
            20                  25                  30

Thr Arg Arg Lys Asn His Asp Asp Thr Cys Arg Arg His Ser Leu Tyr
        35                  40                  45

Val Asp Phe Ser Asp Val Gly Trp Asp Trp Ile Val Ala Pro Leu
     50                  55                  60

Gly Tyr Asp Ala Tyr Tyr Cys His Gly Lys Cys Pro Phe Pro Leu Ala
 65                  70                  75                  80

Asp His Phe Asn Ser Thr Asn His Ala Val Val Gln Thr Leu Val Ala
                85                  90                  95

Asn Asn Met Asn Pro Gly Lys Val Pro Lys Ala Cys Cys Val Pro Thr
                100                 105                 110

Gln Leu Asp Ser Val Ala Met Leu Tyr Leu Asn Asp Gln Ser Thr Val
            115                 120                 125

Val Leu Lys Asn Tyr Gln Glu Met Thr Val Val Gly Cys Gly Cys Arg
        130                 135                 140
```

(2) INFORMATION FOR SEQ ID NO:5:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

```
Arg Thr Thr Arg Ser Ala Ser Ser Arg Arg Gln Gln Ser Arg Asn
1               5                  10                  15

Arg Ser Thr Gln Ser Gln Asp Val Ala Arg Val Ser Ser Ala Ser Asp
                20                  25                  30

Tyr Asn Ser Ser Glu Leu Lys Thr Ala Cys Arg Lys His Glu Leu Tyr
                35                  40                  45

Val Ser Phe Gln Asp Leu Gly Trp Gln Asp Trp Ile Ile Ala Pro Lys
        50                  55                  60

Gly Tyr Ala Ala Asn Tyr Cys Asp Gly Glu Cys Ser Phe Pro Leu Asn
65                  70                  75                  80

Ala His Met Asn Ala Thr Asn His Ala Ile Val Gln Thr Leu Val His
                85                  90                  95

Leu Met Asn Pro Glu Tyr Val Pro Lys Pro Cys Cys Ala Pro Thr Lys
                100                 105                 110

Leu Asn Ala Ile Ser Val Leu Tyr Phe Asp Asp Asn Ser Asn Val Ile
                115                 120                 125

Leu Lys Lys Tyr Arg Asn Met Val Val Arg Ala Cys Gly Cys His
        130                 135                 140
```

(2) INFORMATION FOR SEQ ID NO:6:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

```
Glu Cys Lys Asp Ile Gln Thr Phe Leu Tyr Thr Ser Leu Leu Thr Val
1               5                  10                  15

Thr Leu Asn Pro Leu Arg Cys Lys Arg Pro Arg Arg Lys Arg Ser Tyr
                20                  25                  30

Ser Lys Leu Pro Phe Thr Ala Ser Asn Ile Cys Lys Lys Arg His Leu
        35                  40                  45

Tyr Val Glu Phe Lys Asp Val Gly Trp Gln Asn Trp Val Ile Ala Pro
        50                  55                  60

Gln Gly Tyr Met Ala Asn Tyr Cys Tyr Gly Glu Cys Pro Tyr Pro Leu
65                  70                  75                  80

Thr Glu Ile Leu Asn Gly Ser Asn His Ala Ile Leu Gln Thr Leu Val
                85                  90                  95
```

```
His Ser Ile Glu Pro Glu Asp Ile Pro Leu Pro Cys Cys Val Pro Thr
            100                 105                 110

Lys Met Ser Pro Ile Ser Met Leu Phe Tyr Asp Asn Asn Asp Asn Val
        115                 120                 125

Val Leu Arg His Tyr Glu Asn Met Ala Val Asp Glu Cys Gly Cys Arg
    130                 135                 140
```

(2) INFORMATION FOR SEQ ID NO:7:

(i) SEQUENCE CHARACTERISTICS:
        (A) LENGTH: 147 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

```
Gly Ala Asp Glu Glu Lys Glu Gln Ser His Arg Pro Phe Leu Met Leu
1               5                   10                  15

Gln Ala Arg Gln Ser Glu Asp His Pro His Arg Arg Arg Arg Arg Gly
            20                  25                  30

Leu Glu Cys Asp Gly Lys Val Asn Ile Cys Cys Lys Lys Gln Phe Phe
        35                  40                  45

Val Ser Phe Lys Asp Ile Gly Trp Asn Asp Trp Ile Ile Ala Pro Ser
    50                  55                  60

Gly Tyr His Ala Asn Tyr Cys Glu Gly Glu Cys Pro Ser His Ile Ala
65                  70                  75                  80

Gly Thr Ser Gly Ser Ser Leu Ser Phe His Ser Thr Val Ile Asn His
                85                  90                  95

Tyr Arg Met Arg Gly His Ser Pro Phe Ala Asn Leu Lys Ser Cys Cys
            100                 105                 110

Val Pro Thr Lys Leu Arg Pro Met Ser Met Leu Tyr Tyr Asp Asp Gly
        115                 120                 125

Gln Asn Ile Ile Lys Lys Asp Ile Gln Asn Met Ile Val Glu Glu Cys
    130                 135                 140

Gly Cys Ser
145
```

(2) INFORMATION FOR SEQ ID NO:8:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:8:

```
Gly Met Asn Arg Pro Phe Leu Leu Leu Met Ala Thr Pro Leu Glu Arg
1               5                   10                  15

Ala Gln His Leu Gln Ser Ser Arg His Arg Arg Ala Leu Asp Thr Asn
            20                  25                  30
```

```
Tyr Cys Phe Ser Ser Thr Glu Lys Asn Cys Cys Val Arg Gln Leu Tyr
        35                  40                  45

Ile Asp Phe Arg Lys Asp Leu Gly Trp Lys Trp Ile His Glu Pro Lys
50                  55                  60

Gly Tyr His Ala Asn Phe Cys Leu Gly Pro Cys Pro Tyr Ile Trp Ser
65                  70                  75                  80

Leu Asp Thr Gln Tyr Ser Lys Val Leu Ala Leu Tyr Asn Gln His Asn
            85                  90                  95

Pro Gly Ala Ser Ala Ala Pro Cys Cys Val Pro Gln Ala Leu Glu Pro
                100                 105                 110

Leu Pro Ile Val Tyr Tyr Val Gly Arg Lys Pro Lys Val Glu Gln Leu
            115                 120                 125

Ser Asn Met Ile Val Arg Ser Cys Lys Cys Ser
        130                 135

(2) INFORMATION FOR SEQ ID NO:9:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:9:

Asp Val Leu Glu Asp Ser Glu Thr Trp Asp Gln Ala Thr Gly Thr Lys
1               5                   10                  15

Thr Phe Leu Val Ser Gln Asp Ile Arg Asp Glu Gly Trp Glu Thr Leu
            20                  25                  30

Glu Val Ser Ser Ala Val Lys Arg Trp Val Arg Ala Asp Ser Thr Thr
        35                  40                  45

Asn Lys Asn Lys Leu Glu Val Thr Val Gln Ser His Arg Glu Ser Cys
50                  55                  60

Asp Thr Leu Asp Ile Ser Val Pro Pro Gly Ser Lys Asn Leu Pro Phe
65                  70                  75                  80

Phe Val Val Phe Ser Asn Asp Arg Ser Asn Gly Thr Lys Glu Thr Arg
            85                  90                  95

Leu Asp Leu Leu Lys Glu Met Ile Gly His Glu Gln Glu Thr Met Leu
                100                 105                 110

Val Lys Thr Ala Lys Asn Ala Tyr Gln Gly Ala Gly Glu Ser Gln Glu
            115                 120                 125

Glu Glu Gly Leu Asp Gly Tyr Thr Ala Val Gly Pro Leu Leu Ala Arg
        130                 135                 140

Arg Lys Arg Ser Thr Gly Ala Ser Ser His Cys Gln Lys Thr Ser Leu
145                 150                 155                 160

Arg Val Asn Phe Glu Asp Ile Gly Trp Asp Ser Trp Ile Ile Ala Pro
                165                 170                 175

Lys Glu Tyr Asp Ala Tyr Glu Cys Lys Gly Gly Cys Phe Phe Pro Leu
            180                 185                 190

Ala Asp Asp Val Thr Pro Thr Lys His Ala Ile Val Gln Thr Leu Val
        195                 200                 205
```

His Leu Lys Phe Pro Thr Lys Val Gly Lys Ala Cys Cys Val Pro Thr
    210                 215                 220

Lys Leu Ser Pro Ile Ser Ile Leu Tyr Lys Asp Asp Met Gly Val Pro
225                 230                 235                 240

Thr Leu Lys Tyr His Tyr Glu Gly Met Ser Val Ala Glu Cys Gly Cys
                245                 250                 255

Arg (2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:10:

TGGAATTCTG GVANGAYTGG ATHRTNGC                                    28

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:11:

GAGGATCCAR NGTYTGNACD ATNGCRTG                                    28

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:12:

TGGAATTCAT CGATAACGGA AGCTGAAGC                                   29

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:13:

AGCGTCGACA TCGATATTCA GCATATACTA CC                               32

(2) INFORMATION FOR SEQ ID NO:14:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:14:

GCGAATTCGA TATCAGCTTC TGCTCTGCTC CTATGCTTCT CTTGC          45

(2) INFORMATION FOR SEQ ID NO:15:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (xi) SEQUENCE DESCRIPTION: SEQ ID NO:15:

CGGAATTCGA TATCCGAGGA GGACCTGAAC CACTGTCGGA GAACGTC        47

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Ser Ile Gly Ala Glu Gln Lys Leu Ile Ser
1             5                  10

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Arg Ser Lys Arg
1

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:18:

-continued

```
Glu Gln Lys Leu Ile Ser Glu Glu Asp Leu
1               5                   10
```